(12) United States Patent  
Aitkenhead et al.

(10) Patent No.: US 8,759,774 B2
(45) Date of Patent: Jun. 24, 2014

(54) METHOD AND APPARATUS THAT UTILISES FLUORESCENCE TO DETERMINE PLANT OR BOTANICAL ORIGIN CHARACTERISTICS OF HONEY

(75) Inventors: Catherine Aitkenhead, Auckland (NZ); Douglas Rosendale, Auckland (NZ); Ralf Christian Schlothauer, Tauranga (NZ); Jonathan McDonald Counsell Stephens, Hamilton (NZ)

(73) Assignee: Comvita New Zealand Limited, Te Puke (NZ)

( * ) Notice: Subject to any disclaimer, the term of this patent is extended or adjusted under 35 U.S.C. 154(b) by 0 days.

(21) Appl. No.: 13/990,217

(22) PCT Filed: Nov. 29, 2011

(86) PCT No.: PCT/NZ2011/000248
§ 371 (c)(1),
(2), (4) Date: Jul. 18, 2013

(87) PCT Pub. No.: WO2012/074413
PCT Pub. Date: Jun. 7, 2012

(65) Prior Publication Data
US 2013/0284945 A1    Oct. 31, 2013

(30) Foreign Application Priority Data
Nov. 29, 2010    (NZ) ........................................ 589582

(51) Int. Cl.
G01N 21/64        (2006.01)
(52) U.S. Cl.
CPC .................... G01N 21/6402 (2013.01)
USPC .................................. 250/339.07; 250/339.8
(58) Field of Classification Search
USPC ........................................ 250/339.07, 339.08
See application file for complete search history.

(56) References Cited

U.S. PATENT DOCUMENTS

2008/0292715 A1*  11/2008  Snow et al. .................... 424/539

FOREIGN PATENT DOCUMENTS

EP          1912059 A1    4/2008
WO    2010027286 A1    3/2010

OTHER PUBLICATIONS

Karoui et al. (2007), "The Use of Front Face Fluorescence Spectroscopy to Classify the Botanical Origin of Honey Samples Produced in Switzerland," Food Chemistry 101, p. 314-323.*
Rouff et al. (2005), "Authentication of the Botanical Origin of Honey by Front-Face Fluorescence Spectroscopy. A Preliminary Study," J. Agric. Food Chem. 2005, 53, 1343-1347.*
M.M. Paradkar, J. Irudayaraj (2001), "Discrimination and Classification of Beet and Cane Inverts in Honey by FT-Raman Spectroscopy," Food Chemistry 76 (2001) 231-239.*
Inoue et al. (2005), "Identification of phenolic compound in manuka honey as specific superoxide anion radical scavenger using electron spin resonance (ESR) and liquid chromatography with coulometric array detection," J. Sci. Food Agric. 85: 872-878 (2005).*

(Continued)

Primary Examiner — Casey Bryant
(74) Attorney, Agent, or Firm — Perkins Coie LLP

(57) ABSTRACT

Methods and apparatus are described for the measurement of honey plant origin characteristics via fluorescence.

19 Claims, 10 Drawing Sheets

(56) References Cited

OTHER PUBLICATIONS

Karoui, et al. "The use of front face fluorescence spectroscopy to classify the botanical origin of honey samples produced in Switzerland" Food Chemistry, Elsevier Science Publishers Ltd, GB, vol. 101, No. 1, Aug. 12, 2006, pp. 314-323, XP005754183 ISSN: 0308-8146.
Notification of Transmittal of the International Search Report and the Written Opinion of the International Searching Authority, or the Declaration re International Application No. PCT/NZ2011/000248: date of mailing Mar. 29, 2012, 5 pages.
Written Opinion of the International Searching Authority re International Application No. PCT/NZ2011/000248; date of mailing Mar. 29, 2012, 4 pages.
Ghosh, et al. "A Fluorescence Spectroscopic Study of Honey and Cane Sugar Syrup" Food Sci. Technol. Res., 11(1), 59-62, 2005.
Anklam. "A review of the analytical methods to determine the geographical and botanical origin of honey", Food Chemistry, 1998, vol. 63, (Nov. 21, 1997), pp. 549-562.

\* cited by examiner

METHOD AND APPARATUS THAT UTILISES FLUORESCENCE TO DETERMINE PLANT OR BOTANICAL ORIGIN CHARACTERISTICS OF HONEY

RELATED APPLICATIONS

This application is a 371 national stage application of PCT/NZ2011/000248, filed Nov. 29, 2011. This application claims priority from NZ589582 dated 29 Nov. 2010, the contents of which are incorporated herein by reference.

TECHNICAL FIELD

The application relates to a method and apparatus for honey measurement. More specifically, the application relates to a method and apparatus that utilises fluorescence to determine plant or botanical origin characteristics of honey.

BACKGROUND ART

Honey analysis can be important to determine characteristics of honey such as honey plant or botanical origin, honey contamination and honey that has been processed in ways that influence the purported activity. Determining honey plant origin is of particular interest for quality control purposes e.g. for determining medical grade high activity honey from those with less medical activity. Reassurance of origin is also important as the value of some honeys e.g. manuka honey, may be markedly higher than that of other honey types.

Measuring plant origin characteristics can be difficult, particularly as there are many different measures that can be analysed to measure honey quality. In addition, many of the existing tests can take 24 hours or more before the results are obtained. This delay in receiving results can impact on processing by delaying blending operations and delaying quality control inspections, both of which may impact on processing costs.

It is known that honey will fluoresce. This is understood to be due to the presence of aromatic compounds in the honey (mainly phenolic compounds) that may be excited by light and that then emit light in response to the excitation. One prior art patent publication, WO 2010/027286A1 uses the property of fluorescence to analyse honey but only measures the result using two parameters meaning that much of the valuable characteristic finger print fluorescence of a honey is not visible. This therefore results in incorrect readings or the potential of not obtaining a valid result.

It should be appreciated from the above that it would be useful to have a method and apparatus for at least measuring plant origin characteristics of honey. In particular, a faster method than that of present methods would be useful.

It is acknowledged that the term 'comprise' and grammatical variations thereof may, under varying jurisdictions, be attributed with either an exclusive or an inclusive meaning. For the purpose of this specification, and unless otherwise noted, the term 'comprise' shall have an inclusive meaning.

Further aspects and advantages of the presently described devices and methods will become apparent from the ensuing description that is given by way of example only.

SUMMARY

The application broadly relates to a method and device that uses fluorescence to measure the presence and concentration of key constituents of honey as well as determining the botanical origin of a honey.

In some embodiments there is provided a method for determining the concentration values of key constituent chemicals of honey, including the steps of:
(a) estimating the botanical origin of at least one standard honey sample, by:
  (i) obtaining key constituent chemical concentrations; and
  (ii) assigning the botanical origin as a numerical value on the basis of abundance of chemical compounds characteristic of certain botanical groups;
(b) generating the fluorescence signature of standard honey samples, by:
  (i) exciting a diluted honey sample solution with light of wavelengths over the range 200-700 nm at increasing increments; and
  (ii) measuring the intensity of the fluorescent light emitted from the excited solution over the range 280-650 nm at increasing increments; and
  (iii) measuring the wavelength of the fluorescent light emitted from the excited solution over the range 280-650 nm at increasing increments; and
  (iv) combining excitation and emitted light as 2-dimensional excitation-emission matrix (EEM);
(c) constructing a validated predictive mathematical model from standard honey data, by:
  (i) using the botanical origin value determined in step (a) as the first matrix in a multivariate analysis;
  (ii) using the fluorescence EEM data determined in step (b) as the second matrix in a multivariate analysis;
  (iii) generating a mathematical model using these two matrices; and,
  (iv) establishing a statistical confidence of predictive power of mathematical model with leave-one-out validation process;
(d) generate the fluorescence EEM signature of an unknown honey sample or samples, as outlined in step (b); and
(e) using the unknown honey fluorescence EEM data from step (d) with the validated mathematical model of step (c) to predict and assign concentration values of key constituent chemicals of honey with defined statistical confidence.

In some embodiments there is provided a method for determining the botanical origin of honey including the steps of:
(a) estimating the botanical origin of standard honey samples, by:
  (i) obtaining key constituent chemical concentrations; and
  (ii) assigning the botanical origin as a numerical value on the basis of abundance of chemical compounds characteristic of certain botanical groups;
(b) generating the fluorescence signature of standard honey samples, by:
  (i) exciting a diluted honey sample solution with light of wavelengths over the range 200-700 nm at increasing increments; and
  (ii) measuring the intensity of the fluorescent light emitted from the excited solution over the range 280-650 nm at increasing increments; and
  (iii) measuring the wavelength of the fluorescent light emitted from the excited solution over the range 280-650 nm at increasing increments; and
  (iv) combining excitation and emitted light as 2-dimensional excitation-emission matrix (EEM);
(c) constructing a validated predictive mathematical model from standard honey data, by:

(i) using the botanical origin value determined in step (a) as the first matrix in a multivariate analysis;
(ii) using the fluorescence EEM data determined in step (b) as the second matrix in a multivariate analysis;
(iii) generating a mathematical model using these two matrices; and,
(iv) establishing a statistical confidence of predictive power of mathematical model with leave-one-out validation process;
(d) generate the fluorescence EEM signature of an unknown honey sample or samples, as outlined in step (b); and
(e) using the unknown honey fluorescence EEM data from step (d) with the validated mathematical model of step (c) to predict and assign numerical value of botanical origin of honey with defined statistical confidence.

In some embodiments there is provided a device for identifying honey botanical origin and/or chemical constituents that includes a sample receiving area into which a honey sample is inserted and the device subsequently identifies the honey botanical origin and chemical constituents via the method as claimed in any one of the above claims.

The methods and device provide a fast and simple way to quickly determine at least qualitatively the botanical origin of a honey sample. This is useful for a variety of reasons including for quality control and to ensure correct labelling of honey as to the source. The methods and device also measure the full characteristic fingerprint of a honey including peaks at varying excitation and emission wavelengths that are missed if only one wavelength (excitation or emission) is measured.

DESCRIPTION OF THE FIGURES

Further aspects of the application will become apparent from the following description that is given by way of example only and with reference to the accompanying drawings in which.

DETAILED DESCRIPTION

Figure 1:
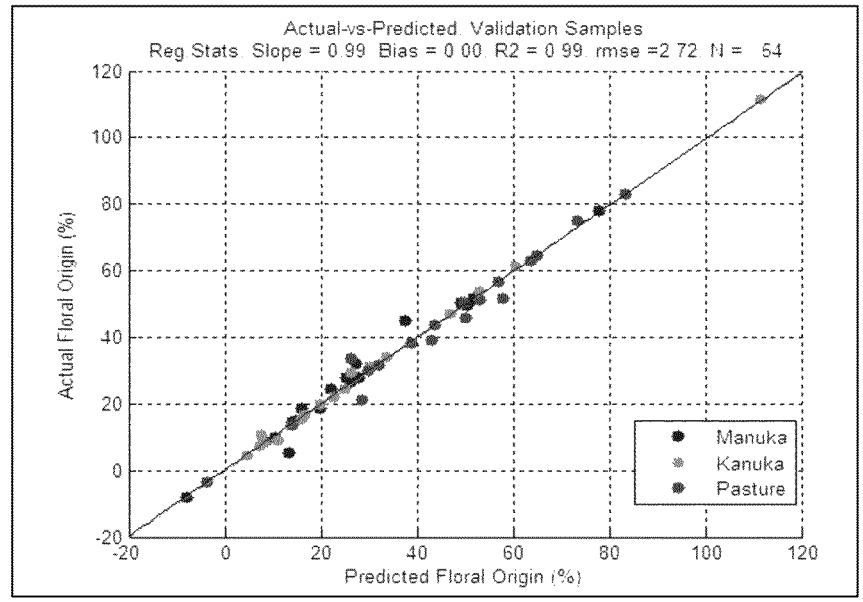
FIG. 1 shows a graph comparison of trained model ('actual') data with predicted data for the independent validation honey samples.

As noted above, the application broadly relates to a method and device that uses fluorescence to measure the presence and concentration of key constituents of honey as well as determining the botanical origin of a honey.

For the purposes of this specification, the term 'fluorescence' and grammatical variations thereof refers to the emission of light by honey that has absorbed light or any electromagnetic radiation of a different wavelength.

The term 'honey' refers to naturally produced honey containing at least a mix of glucose, fructose, water and glucose oxidase enzyme as well as plant derived compounds including aromatic phenolic compounds.

The term 'honey type' refers to a honey from a particular plant origin or a blend of plant origins.

The term 'plant origin' and 'botanical origin' are used interchangeably and refer to the plant nectar that the honey is derived from as evidenced by the specific compound(s) present in the honey that are derived from the plant.

The term 'intensity' refers to how intense the emission of energy is form the honey sample. A high intensity refers to release of high levels of energy relative to general levels. More specifically, the term high intensity refers to the energy level being greater than 30%, 40%, 50%, 60%, 70%, 80%, 90%, or 100% higher than a baseline energy level such as that observed for a low phenolic concentration honey, one example being clover honey.

The term 'peak' refers to a maximum emission intensity expressed as a range in the case of a wide range of wavelengths or a point in the case of a specific wavelength or wavelengths.

The term 'excitation' and grammatical variations thereof refers to the use of electromagnetic radiation elevate the energy level of the molecules and atoms in a honey sample from a ground state.

The term 'emission' and grammatical variations thereof refers to the relative intensity of electromagnetic radiation of any wavelength emitted by the honey compound's molecules when they return to a ground state after being moved to an excited state.

The term 'purity' refers to the honey being a monofloral honey.

The term 'monofloral honey' refers to the honey being predominantly derived from one plant species.

In some embodiments there is provided a method for determining the concentration values of key constituent chemicals of honey, including the steps of:
(a) estimating the botanical origin of at least one standard honey sample, by:
 (i) obtaining key constituent chemical concentrations; and
 (ii) assigning the botanical origin as a numerical value on the basis of abundance of chemical compounds characteristic of certain botanical groups;
(b) generating the fluorescence signature of standard honey samples, by:
 (i) exciting a diluted honey sample solution with light of wavelengths over the range 200-700 nm at increasing increments; and
 (ii) measuring the intensity of the fluorescent light emitted from the excited solution over the range 280-650 nm at increasing increments; and
 (iii) measuring the wavelength of the fluorescent light emitted from the excited solution over the range 280-650 nm at increasing increments; and
 (iv) combining excitation and emitted light as 2-dimensional excitation-emission matrix (EEM);
(c) constructing a validated predictive mathematical model from standard honey data, by:
 (i) using the botanical origin value determined in step (a) as the first matrix in a multivariate analysis;
 (ii) using the fluorescence EEM data determined in step (b) as the second matrix in a multivariate analysis,
 (iii) generating a mathematical model using these two matrices; and,
 (iv) establishing a statistical confidence of predictive power of mathematical model with leave-one-out validation process;
(d) generate the fluorescence EEM signature of an unknown honey sample or samples, as outlined in step (b); and
(e) using the unknown honey fluorescence EEM data from step (d) with the validated mathematical model of step (c) to predict and assign concentration values of key constituent chemicals of honey with defined statistical confidence.

In some embodiments there is provided a method for determining the botanical origin of honey including the steps of:
(a) estimating the botanical origin of standard honey samples, by:
 (i) obtaining key constituent chemical concentrations; and
 (ii) assigning the botanical origin as a numerical value on the basis of abundance of chemical compounds characteristic of certain botanical groups;
(b) generating the fluorescence signature of standard honey samples, by:
 (i) exciting a diluted honey sample solution with light of wavelengths over the range 200-700 nm at increasing increments; and
 (ii) measuring the intensity of the fluorescent light emitted from the excited solution over the range 280-650 nm at increasing increments; and
 (iii) measuring the wavelength of the fluorescent light emitted from the excited solution over the range 280-650 nm at increasing increments; and
 (iv) combining excitation and emitted light as 2-dimensional excitation-emission matrix (EEM);
(c) constructing a validated predictive mathematical model from standard honey data, by:
 (i) using the botanical origin value determined in step (a) as the first matrix in a multivariate analysis;
 (ii) using the fluorescence EEM data determined in step (b) as the second matrix in a multivariate analysis;
 (iii) generating a mathematical model using these two matrices; and,
 (iv) establishing a statistical confidence of predictive power of mathematical model with leave-one-out validation process;
(d) generate the fluorescence EEM signature of an unknown honey sample or samples, as outlined in step (b); and
(e) using the unknown honey fluorescence EEM data from step (d) with the validated mathematical model of step (c) to predict and assign numerical value of botanical origin of honey with defined statistical confidence.

In the above embodiments, the numerical value of botanical origin may be expressed as a percentage manuka honey, percentage kanuka honey, percentage other specific floral origin honey, percentage other origin honey as a sum, and combinations thereof.

The constituent chemicals in a honey and/or the honey floral origin may be determined instead by analysis of the nectar from which the honey is derived.

In the above methods, the fluorescence signature may be generated using excitation wavelengths in the range 200-700 nm. Alternatively, the fluorescence signature may be generated using the key excitation wavelengths, 230 nm, 265 nm, and 335 nm. As may be appreciated, use of three or four excitation wavelengths instead of full EEM scanning is potentially simpler and cheaper to complete and may be preferable where a portable instrument for use in the field is to be produced.

For the purposes of this specification, the term 'standard honey sample' or grammatical variations thereof may be those honeys for which prior knowledge of honey age and/or one or more chemical constituents exists. Traditional methods of analysis of phenolic content may be by use of separation via high performance liquid chromatography (HPLC) followed by UV or fluorescence detection and comparison with a known standard. Alternatively, traditional methods of analysis may include HPLC followed by mass spectroscopy (HPLC-MS) to separate and identify compounds. As may be appreciated, the above traditional methods of analysis require specialised and expensive equipment (and the equipment is typically not portable). Specialised knowledge to operate the equipment is also required and specialist software tools are needed to analyse the results. In addition, some compounds require different processing prior to the above HPLC analyses further exacerbating the complexity of the analysis process.

The key constituent chemicals may include compounds selected from: methyl syringate, 2-methoxybenzoic acid, phenyllactic acid, 4-methoxyphenyllactic acid, dihydroxyacetone (DHA), methylglyoxal (MGO), and combinations thereof. Compounds listed are known to be markers of botanical origin for at least some common types of honey. Absence of or higher concentrations of these compounds signify particular honey origins. In addition MGO is known to be directly attributable to the UMF or antibacterial activity of a honey hence is a common marker of honey value and widely used in honey labelling. DHA is a precursor compound to MGO and over time converts to MGO hence is also a key marker compound in honey.

As may be appreciated, the correlation between the phenolic profiles and levels of the antimicrobial (UMF®) molecule MGO and its precursor DHA was quite unexpected. Phenolic compounds fluoresce due to the presence of or one or more aromatic rings in the chemical structure. The compounds DHA and MGO are comparatively simple compounds that do not directly fluoresce. The applicants found that accurate predictions of DHA and MGO concentrations could be measured by analysis of the phenolic concentrations and insertion into the model. It appears that one or more marker phenolic compounds (e.g. 2-methoxybenzoic acid) in honey directly correlates to the presence of DHA and/or MGO. The applicants have identified that the DHA content is directly proportional to the phenolic concentrations or at least selected manuka honey characteristic levels. This relationship also unexpectedly stays proportional over time as both the phenolic concentration and the DHA concentration decay at the same exponential (Arrhenius) rate. The same rate of decay is surprising as other compounds such as MGO does not decay in the same manner. Known correlations from the art describe the correlation between DHA and MGO concentration hence, if the DHA level is known, the MGO and/or UMF activity may also be calculated.

The ability to measure DHA and MGO contents is particularly useful as MGO levels (responsible for the UMF® activity of some honeys) are attributable to the antimicrobial activity of so called 'active' or medical honeys. High UMF/MGO concentration honeys typically attract greater monetary value hence there is some need to quickly measure and determine that the label or stated MGO/UMF level is in fact correct. Adulterating the MGO/UMF level is relatively simple to obtain a higher value honey yet, adulteration may in fact leave behind undesirable compounds—one example being heating of honey which leaves behind unwanted HMF compounds. Note also that DHA is a precursor compound to MGO and in time, DHA converts to MGO hence also knowing DHA levels adds to the overall analysis.

The leave-one-out validation process may involve re-creating the model in the absence of selected standard honey data, and then entering standard honey fluorescence data as unknown honey to predict botanical origin and chemical constituent concentrations, and determining statistical variance from known values. In some embodiments the mathematical model used may be a partial least squares (PLS) analysis. THE PLS may be an N-way PLS (NPLS) method.

As may be appreciated, the above methods may be completed for a wide variety of reasons. In some embodiments, if the determined key constituent concentration and/or botanical origin of the unknown honey or honeys do not agree with the labelling affixed to a honey, the honey may be rejected and not processed. In alternative embodiments, the methods may be used to determine the monetary value of the honey based on the botanical origin purity and/or chemical constituents. In other embodiments, the methods may be used to characterise honeys on the basis of chemical constituents that may have biological activity including, but not limited to, antimicrobial, antioxidant, immunomodulatory or neuroendocrine activities. In other embodiments, the methods may be used to characterise honeys for use as standard mixtures for calibration purposes for the fluorescence profile comparison of other, unrelated mixtures. In other embodiments, the methods may be used to characterise honeys on the basis of seasonal or climatic variation, flowering time, rainfall or wind patterns or alternative environmental concerns which alter the availability and composition of the nectar from which the honey is derived. In further embodiments, the former characterisation might be used to generate calibration standards or biomarkers for the comparison of these environmental factors. In other embodiments, the methods may be used to characterise honeys on the basis of bee or hive status which may impact on either collection of nectar from which the honey is derived, or on the condensation process which occurs within the hive, from which the honey is derived. In further embodiments, the former characterisation might be used to generate calibration standards or biomarkers for the comparison of these bee or hive factors.

The sample or samples may be initially diluted to a 0.2 to 5% w/v solution using water. The sample or samples may be initially diluted to an approximately 0.5%, 0.75%, 1.0%, 1.25%. 1.5%. 1.75%. 2.0%. 2.25%, 2.5%, 2.75%, 3.0%, 3.25%, 3.5%, 3.75%, 4.0%, 4.25%, 4.5%, 4.75% w/v solution using water. The dilution may be approximately 2% w/v. The applicants have determined that the level of dilution is important to obtaining an accurate result. If the concentration is too low or too high the accuracy of the method decreases dramatically. The term approximately is used above and refers to the amount described varying by 1%, 2%, 5%, 10%, 15% or 20% from that stated. The water may ideally be sterilised and/or deionised.

The sample or samples may include a dye that provides a control intensity and frequency of fluorescence. In some embodiments, the dye may be Alexa Fluor™ dye 594 that emits at 625 nm although it should be appreciated that other dyes may also be used that fluoresce outside the range of that measured. Alexa Fluor dye is advantageous as it not only fluoresces outside the range analysed but also is sufficiently stable to not photo bleach in light or deteriorate in heat at any appreciable rate. In some embodiments, the dye or dyes used are sufficiently light stable so as to not photo bleach when stored in light in a diluted state over a time period of 4 hours.

Alternatively, the dye may be replaced with quantum dots instead for use as a standard. In further embodiments both a dye or dyes and quantum dots may be used.

The applicants have found that the higher the peak intensity of the measured sample, the greater the botanical origin purity or monofloral nature of the sample. This is particularly the case for *Leptospermum* and *Kunzea* genus plant origin honeys although this may also be the case with other botanical origin honeys and the methods may be used to at least accurately distinguish the floral purity or concentration *Leptospermum* genus, *Kunzea* genus and collectively other variety plant origin honeys.

For the purposes of this specification reference to *Leptospermum* genus plants includes manuka however, this should not be seen as limiting as other *Leptospermum* species have similar phenolic compounds and hence results found for manuka species are also observed for other *Leptospermum* Species.

For the purposes of this specification reference to *Kunzea* genus plants includes kanuka however, this should not be seen as limiting as other *Kunzea* species have similar phenolic compounds and hence results found for kanuka species are also observed for other *Kunzea* species.

To further illustrate the nature of the results obtained from analysis, a variety of characteristics excitation wavelengths and peak intensities are provided for varying honey floral origins. The figures provided should be seen as trends and the actual figures may vary up to 10 to 20% from that illustrated. It should further be noted that the analysis described in the above claims tends to place more weight on qualitative trends as opposed to the quantitative figures below. As a result, specific peaks or frequencies described, whilst being important to the overall results are used to provide trends in determining the overall results.

Peak intensity above 30,000 may indicate the presence of either *Leptospermum* genus, *Kunzea* genus origin honey or both honeys.

Peak intensity at 270 nm and 340 nm excitation corresponding to 380 nm, 440 nm and 490 nm emission may indicate the presence of *Leptospermum* genus origin honey.

If a maximum intensity above 30,000 exists and there is no peak wavelength located at 230 nm excitation and 310 nm emission, the honey may be *Leptospermum* genus honey.

If a maximum intensity between 10,000 and 30,000 exists and the highest or second highest peak is located at 270 nm excitation and 370-380 nm emission and there are two small peaks at 340 nm excitation and there is no peak located at 230 nm excitation and 310 nm emission, the honey may be a *Leptospermum* genus honey blended with other honey.

If the peak intensity occurs at 230 nm, 280 nm and 270 nm excitation corresponding to 310 nm and 380 nm emission, the honey may be *Kunzea* genus origin honey.

If a maximum intensity above 30,000 exists and there is a peak wavelength located at 230 nm excitation and 310 nm emission, the honey is of *Kunzea* genus origin.

In the case of *Kunzea* genus origin, a phenolic compound, the applicants have identified 4-methoxyphenyl lactic acid, as the phenolic compound that fluoresces at 230 nm excitation and 310 nm emissions. This is a compound that is mainly found within kanuka origin honeys. It is anticipated that other plant origin specific compounds will eventually be identified corresponding to the various peaks and emission frequencies observed.

If a maximum intensity between 10,000 and 30,000 exists and the highest or second highest peak is located at 270 nm excitation and 370-380 nm emission and there are two small peaks at 340 nm excitation and a peak located at 230 nm excitation and 310 nm emission, the honey may be a blend of both *Leptospermum* genus and *Kunzea* genus honey.

If the maximum intensity is below 10,000 and there are two distinct peaks where the trough is greater than half the peak height and the peaks are above 5,000, the honey may be either *Trifolium* genus or *Weinmannia silvicola* species honey.

For the purposes of this specification reference to *Trifolium* genus plants includes clover however, this should not be seen as limiting as other *Trifolium* species have similar phenolic compounds and hence results found for clover species are also observed for other *Trifolium* species.

For the purposes of this specification reference to *Weinmannia silvicola* species plants includes towai however, this should not be seen as limiting as other *Weinmannia silvicola* species have similar phenolic compounds and hence results found for towai species are also observed for other *Weinmannia silvicola* species.

Peak intensity at approximately 230 nm, 280 nm and 260 nm excitation corresponding to 310 nm, 360 nm and 490 nm emission may indicate that the sample may be *Weinmannia silvicola* species origin honey.

If a peak exists at 350 nm emission, the honey may be of *Trifolium* genus or *Ixerba* genus origin.

For the purposes of this specification reference to *Ixerba* genus plants includes tawai however, this should not be seen as limiting as other *Ixerba* genus plants have similar phenolic compounds and hence results found for tawari species are also observed for other *Ixerba* genus plants.

A peak intensity at approximately 280 nm and 230 nm excitation corresponding to 350 nm emission indicates that the sample is *Ixerba* genus or *Trifolium* genus origin honey.

If the maximum intensity is below 10,000 and there are two distinct peaks where the trough is greater than half the peak height and the peaks are below 5,000, the honey may be of *Ixerba* genus origin.

A peak intensity at approximately 280 nm, 230 nm and 250 nm excitation corresponding to 360 nm, 370 nm and 490 nm emission may indicate *Metrosideros excelsa* origin honey.

For the purposes of this specification reference to *Metrosideros excelsa* species plants includes pohutukawa however, this should not be seen as limiting as other *Metrosideros excelsa* species plants have similar phenolic compounds and hence results found for pohutukawa species are also observed for other *Metrosideros excelsa* species.

If the maximum intensity is below 10,000 and there are three distinct peaks where the trough is greater than half the peak height with intensity above 2,000, the honey may be of *Metrosideros excelsa* origin.

If the maximum intensity is below 10,000 and there are more four or more distinct peaks where the trough is greater than half the peak height, the honey may be selected from *Metrosideros* genus, *Weinmannia* genus or *Knightea* genus honey.

For the purposes of this specification reference to *Metrosideros* genus species plants includes rata however, this should not be seen as limiting as other *Metrosideros* genus species plants have similar phenolic compounds and hence results found for rata species are also observed for other *Metrosideros* genus species.

For the purposes of this specification, reference to *Weinmannia* genus species plants includes kamahi however, this should not be seen as limiting as other *Weinmannia* genus species plants have similar phenolic compounds and hence results found for kamahi species are also observed for other *Weinmannia* genus species.

For the purposes of this specification, reference to *Knightea* genus species plants includes rewarewa however, this should not be seen as limiting as other *Knightea* genus species plants have similar phenolic compounds and hence results found for rewarewa species are also observed for other *Knightea* genus species.

A peak intensity at approximately 270 nm, 260 nm, 230 nm and 260 nm excitation corresponding to 370 nm, 490 nm, 380 nm and 450 nm emission may indicate *Metrosideros* genus origin honey.

If the maximum intensity is above 10,000 and there are more four or more distinct peaks where the trough is greater than half the peak height, the honey may be *Nothofagus* genus or *Knightea* genus honey.

For the purposes of this specification, reference to *Nothofagus* genus species plants includes beech however, this should not be seen as limiting as other *Nothofagus* genus species plants have similar phenolic compounds and hence results found for beech species are also observed for other *Nothofagus* genus species.

A peak intensity at approximately 270 nm and 230 nm excitation corresponding to 370 nm and 380 nm emission may indicate *Knightea* genus origin honey.

If peak intensity exists of approximately 10,000 at scan coordinates 270 nm and 230 nm excitation corresponding to 370 nm and 380 nm emission, the honey may be of *Knightea* genus origin.

Peak intensity at approximately 290 nm and 230 nm excitation corresponding to 390 nm and 400 nm emission may indicate *Nothofagus* genus origin honey.

Peak intensity at approximately 280 nm, 230 nm 240 nm and 260 nm excitation corresponding to 360 nm, 390 nm, 440 nm and 490 nm emission may indicate *Weinmannia* genus origin honey.

As should be appreciated, variation in the figures provided may occur without departing from the scope of the embodiments described herein. As a general rule, the fluorescent wavelength may vary plus or minus 5 nm, 10 nm, 15 nm, 20 nm, 25 nm, 30 nm, 35 nm or 40 nm from the stated figure however, the trends and standards described still hold true and may be used to at least qualitatively identify the various species origins of the honey sample(s).

Manipulations to honey may also be measured or inferred from the above method. Manipulations to honey may be for a variety of reasons. Manipulations may include addition of DHA or MGO in order to manipulate the MGO level. Alternatively, manipulations may include heating of the honey and/or pH adjustment. Since these manipulations can artificially increase the monetary value of a honey, knowing whether or not manipulation has occurred may be of considerable importance.

In some embodiments there is provided a device for identifying honey botanical origin and/or chemical constituents that includes a sample receiving area into which a honey sample is inserted and the device subsequently identifies the honey botanical origin and chemical constituents via the methods substantially as hereinbefore described.

As should be appreciated from the above description, after analysis to optimise the method settings and results, it was found to be possible to distinguish between honey samples from different botanical origin and to determine the chemical concentration of selected constituents in the honey. The analysis of a honey sample is based on its fluorescence intensity, the location of peaks and optionally, the ratio of peak heights and the ratio of slopes. Excitation and fluorescence is possible due in part to the aromatic nature of the phenolic compounds present in honey. These aromatic compounds are derived from the plant species that the honey is produced from and the specific phenolic compounds vary depending on the plant species. In effect, the aromatic phenolic compounds leave a chemical fingerprint in the honey showing which plant species the honey is derived from. Analysing honey for plant species origin has been possible but typically tests are slow. The present methods and device provide means to rapidly obtain at least a qualitative determination of the honey origin. With refinement, the methods and device may also potentially be used to quantitatively determine the honey plant origin and composition. The methods and device may also be used in conjunction with more traditional tests, for example where the first fluorescence scan is not totally clear as to the origin.

Further details are provided in the working examples below.

WORKING EXAMPLES

The application is now described with reference to examples illustrating embodiments of the methods and device.

Example 1

In this example, a model to predict honey compound concentration and botanical origin was produced, validated and tested against unknown honey samples.

Seventy-five honey samples were collected accompanied by some composition data and estimates of floral origin.

The honey samples were diluted to a 2% (w/v) solution in a 0.05% solution of fluorescent dye (Alexa Dye 594) in deionised water. Blends of the honey solutions were made by mixing two diluted honeys together in even volumes.

The fluorescence of honey was measured using a Tecan XFLUOR4 SAFIRE II (Tecan Austria GmbH, Austria).

Black (100 μL well volume) 384-well plates were used for each scan. Black plates were used because white plates reflect fluorescent rays and transparent plates transmit light from adjacent wells. These deep well plates were used to minimise the effects of evaporative sample loss.

The measurement mode used was the fluorescence top 3D scan. The integration was 2000 μs with the flash mode set to high sensitivity. The gain was set at 85 and the z position at 10,622 μm. The range of excitation wavelengths was between 230 and 400 nm, while the emission scans ranged from 280 to 650 nm. Readings were taken at increasing 5 nm increments in both the emission and excitation ranges.

When the excitation and emission wavelengths of honey samples overlapped there was an apparent significant fluorescent output. This is not fluorescence from the samples, but an artefact of the photomultiplier detecting the excitation light. This artefact has been subtracted from the analyses.

Data Pre-Processing

The raw data from the Tecan XFLUOR4 SAFIRE II are presented in an Excitation-Emission Matrix (EEM) for each sample. All samples that were analysed contain an internal standard to eliminate the effects of evaporation. The internal standard used was Alexa Fluor 594 Dye, which has a fluorescent spectrum that does not overlap with the fluorescent spectrum of the honey. To remove evaporative losses that affect the data, points were adjusted so that the data points are still in the same ratios to one another. The peak chosen as the baseline was located at 265 nm excitation and 615 nm emission, which was set to 10,000 in all samples. All of the points were changed accordingly by dividing each data point by the value of the set peak in the raw data, and multiplying the result by 10,000.

Once the data had been normalised, the fluorescent data of a blank sample was removed so that the background fluorescence due to the solvent and the dye could not be seen. The blank sample was scanned as if it were one of the honey samples, but it only contained the solvent (water) and dye. The data were also pre-processed, as stated, so the peak was set to 10,000.

Data Analysis

MATLAB® (Version 7.8.0.347, Mathworks, USA) and the associated PLS_Toolbox (Version 6.1, Eigenvector Research Inc., USA) were used to process the data and construct predictive models. PLS_Toolbox contains a large array of multivariate data analysis techniques, with the principal ones involving the method of partial least squares (PLS) analysis or N-way PLS (termed NPLS). As the PLS_Toolbox runs under the MATLAB programming environment, a general purpose analysis Graphical User Interface (GUI) was used for all of the modelling, and general MATLAB functions were only used to import and prepare the data prior to loading into the Analysis GUI.

NPLS handles and processes data that are presented in two or more spectral dimensions. This makes NPLS a highly appropriate analysis tool as the EEM data consist of two spectral dimensions—the excitation and emission wavelengths.

To judge the performance of a model, it must be applied to evaluate new samples. Therefore, so that predictions could be made and the model justified, some measured samples were deliberately excluded from the modelling exercise and were subsequent re-entered as unknowns to evaluate the predictive model. Unknown fluorescent data can be loaded into this toolbox as the x data to predict compositional data.

Results

Creating the Predictive Model

Using the PLS Toolbox, a model was created based on NPLS analysis. This model was generated using the base set of 75 samples and a set of 114 blends of honey. Larger samples make for more accurate predictions so blends were made to increase the number of samples available in the training set, as analysis occurs and predictions were made, based on differences between fluorescent data.

TABLE 1

A summary of the estimates of compositional data of the honey samples tested.
Samples include honeys 101-135 and 158-175.
Samples 136-157 lacked the chemical compositional data required to estimate floral origin.

| Sample Number | Type | Manuka (%) | Kanuka (%) | Pasture (%) |
|---|---|---|---|---|
| 101 | Manuka | 75 | 0 | 25 |
| 102 | Manuka | 85 | 0 | 15 |
| 103 | Manuka | 62 | 0 | 38 |
| 104 | Manuka | 32 | 0 | 68 |
| 105 | Manuka | 61 | 0 | 39 |
| 106 | Manuka | 92 | 0 | 8 |
| 107 | Manuka | 32 | 0 | 68 |
| 108 | Manuka | 99 | 0 | 1 |
| 109 | Manuka | 80 | 0 | 20 |
| 110 | Manuka | 61 | 0 | 39 |
| 111 | Manuka | 56 | 2 | 42 |
| 112 | Manuka | 95 | 2 | 3 |
| 113 | Manuka | 57 | 5 | 38 |
| 114 | Manuka | 66 | 2 | 32 |
| 115 | Manuka | 75 | 2 | 23 |
| 116 | Manuka | 91 | 0 | 9 |
| 117 | Manuka | 59 | 2 | 39 |
| 118 | Manuka | 78 | 0 | 22 |
| 119 | Manuka | 93 | 0 | 7 |
| 120 | Manuka | 75 | 0 | 25 |
| 121 | Manuka | 73 | 0 | 27 |
| 122 | Kanuka | 5 | 70 | 25 |
| 123 | Kanuka | 5 | 30 | 65 |
| 124 | Kanuka | 5 | 25 | 70 |
| 125 | Kanuka | 5 | 30 | 65 |
| 126 | Kanuka | 5 | 90 | 5 |
| 127 | Kanuka | 10 | 85 | 5 |
| 128 | Kanuka | 5 | 90 | 5 |
| 129 | Kanuka | 10 | 85 | 5 |
| 130 | Kanuka | 5 | 80 | 15 |
| 131 | Kanuka | 10 | 85 | 5 |
| 132 | Kanuka | 5 | 50 | 45 |
| 133 | Kanuka | 20 | 20 | 60 |
| 134 | Kanuka | 10 | 50 | 40 |
| 135 | Kanuka | 10 | 40 | 50 |
| 158 | Manuka | 10 | 24 | 66 |
| 159 | Manuka | 20 | 21 | 59 |
| 160 | Manuka | 21 | 22 | 57 |
| 161 | Manuka | 14 | 34 | 53 |
| 162 | Manuka | 14 | 29 | 57 |
| 163 | Manuka | 16 | 33 | 51 |
| 164 | Manuka | 25 | 48 | 27 |
| 165 | Manuka | 26 | 53 | 22 |
| 166 | Manuka | 19 | 41 | 40 |
| 167 | Manuka | 18 | 43 | 39 |
| 168 | Manuka | 39 | 25 | 36 |
| 169 | Manuka | 26 | 11 | 63 |
| 170 | Manuka | 32 | 14 | 54 |
| 171 | Manuka | 37 | 15 | 48 |
| 172 | Manuka | 50 | 12 | 39 |
| 173 | Manuka | 58 | 5 | 37 |
| 174 | Manuka | 78 | 2 | 20 |
| 175 | Manuka | 80 | 5 | 15 |

This model used four Latent Variables (LV) that accounted for more than 99% of the fluorescent data. An LV is a variable that is inferred using mathematical models to reduce the dimensionality of the data. The honey samples had known estimates of the percentage composition (manuka, kanuka and pasture) of some of the honeys based on prior knowledge of honey composition (Table 1). This was compared to the fluorescent data. The PLS_Toolbox predicts sample composition based on differences calculated from the fluorescent data. Therefore, the Toolbox was able to compare the estimated values with its predictions. The predictions were then loaded back into the model as the estimated compositional data until the model accounted for more than 99% of the variance of the composition data, as well as fluorescent data (Table 2).

Some of the honey samples used omitted phenolic composition data so relative floral (nectar) composition could not be estimated. However, a general description of their floral origin was supplied, and so these honeys were initially entered as being 100% from that source. The predictions made by the Toolbox when compared with the measured values were again reloaded into the model until more than 99% of the compositional data were accounted for.

To extend the library of honey samples, diluted blends of the original honeys were scanned and the EEM were generated. The composition data were calculated from the relative proportions of values from each of the mixed honeys. This provided a model that accounted for more than 99% of the fluorescent data and 97% of the composition data. As the model makes predictions based on differences in the spectra, a change in the compositional data entered will change the predictions slightly, with each cycle giving a more accurate prediction. Therefore, the predictions were reloaded as the measured compositional data so that the model accounted for more than 99% of the fluorescent and composition data (Table 3).

TABLE 2

Predicted floral composition of honey samples used.
Samples include honeys 101-188.

| Sample Number | Type | Manuka (%) | Kanuka (%) | Pasture (%) |
|---|---|---|---|---|
| 101 | Manuka | 51.55 | 6.71 | 41.72 |
| 102 | Manuka | 58.16 | 5.03 | 36.81 |
| 103 | Manuka | 53.79 | 6.14 | 40.05 |
| 104 | Manuka | 24.59 | 3.73 | 71.69 |
| 105 | Manuka | 49.40 | 7.25 | 43.34 |
| 106 | Manuka | 63.20 | −6.43 | 43.29 |
| 107 | Manuka | 30.29 | 3.22 | 66.49 |
| 108 | Manuka | 122.72 | 5.73 | −28.54 |
| 109 | Manuka | 92.45 | 10.82 | −3.36 |
| 110 | Manuka | 78.06 | 8.02 | 13.85 |
| 111 | Manuka | 40.43 | 3.34 | 56.24 |
| 112 | Manuka | 80.29 | −5.62 | 25.33 |
| 113 | Manuka | 44.35 | 6.25 | 49.41 |
| 114 | Manuka | 70.06 | −2.75 | 32.69 |
| 115 | Manuka | 82.33 | 2.48 | 15.16 |
| 116 | Manuka | 63.70 | 17.08 | 19.03 |
| 117 | Manuka | 38.66 | 21.92 | 39.29 |
| 118 | Manuka | 60.10 | 18.47 | 21.25 |
| 119 | Manuka | 32.92 | 9.97 | 57.08 |
| 120 | Manuka | 27.87 | 7.33 | 64.78 |
| 121 | Manuka | 33.01 | 7.11 | 59.87 |
| 122 | Kanuka | 16.16 | 25.50 | 58.32 |
| 123 | Kanuka | 6.50 | 29.98 | 63.47 |
| 124 | Kanuka | 9.96 | 28.43 | 61.59 |
| 125 | Kanuka | 8.32 | 28.59 | 63.05 |
| 126 | Kanuka | −4.70 | 101.71 | 2.99 |
| 127 | Kanuka | 4.47 | 100.99 | −5.43 |
| 128 | Kanuka | 22.13 | 69.36 | 8.54 |
| 129 | Kanuka | −4.08 | 108.50 | −4.40 |
| 130 | Kanuka | −8.16 | 111.49 | −3.32 |
| 131 | Kanuka | −2.40 | 115.06 | −12.63 |
| 132 | Kanuka | −7.27 | 59.34 | 47.89 |
| 133 | Kanuka | 26.28 | 38.83 | 34.90 |
| 134 | Kanuka | 10.81 | 30.24 | 58.94 |
| 135 | Kanuka | 3.28 | 40.70 | 56.00 |
| 136 | Kamahi | 10.78 | 10.77 | 78.45 |
| 137 | Kamahi | 12.10 | 8.30 | 79.59 |
| 138 | Towai | 7.25 | 20.24 | 72.48 |
| 139 | Rata | 9.53 | 9.41 | 81.05 |
| 140 | Pohutukawa | 8.74 | 8.39 | 82.85 |
| 141 | Clover | 6.87 | 16.79 | 76.31 |
| 142 | Clover | 9.71 | 11.09 | 79.19 |
| 143 | Tawari | 6.93 | 9.47 | 83.58 |
| 144 | Rewarewa | 13.67 | 5.62 | 80.71 |
| 145 | Rewarewa | 18.71 | 14.14 | 67.14 |
| 146 | Rewarewa | 18.97 | 6.31 | 74.72 |
| 147 | Honeydew | 28.97 | 10.14 | 60.93 |
| 148 | Honeydew | 21.27 | 11.67 | 67.08 |
| 149 | Kanuka | 17.77 | 64.67 | 17.48 |
| 150 | Kanuka | 14.27 | 47.28 | 38.40 |
| 151 | Kanuka | 2.16 | 88.97 | 8.84 |
| 152 | Kanuka | 8.48 | 77.74 | 13.74 |
| 153 | Kanuka | 7.81 | 64.18 | 27.95 |
| 154 | Kanuka | 2.88 | 83.65 | 13.45 |
| 155 | Kanuka | 8.84 | 57.38 | 33.74 |
| 156 | Kanuka | 12.87 | 73.05 | 14.08 |
| 157 | Kanuka | 4.72 | 85.36 | 9.94 |
| 158 | Manuka | 23.39 | 21.63 | 54.96 |
| 159 | Manuka | 24.71 | 20.11 | 55.18 |
| 160 | Manuka | 26.46 | 16.77 | 56.76 |
| 161 | Manuka | 24.26 | 41.40 | 34.31 |
| 162 | Manuka | 25.49 | 33.33 | 41.16 |
| 163 | Manuka | 28.58 | 31.84 | 39.57 |
| 164 | Manuka | 15.72 | 45.67 | 38.59 |
| 165 | Manuka | 19.04 | 43.86 | 37.08 |
| 166 | Manuka | 22.83 | 35.69 | 41.46 |
| 167 | Manuka | 19.27 | 39.18 | 41.54 |
| 168 | Manuka | 52.26 | 16.42 | 31.34 |
| 169 | Manuka | 42.31 | 8.75 | 48.97 |
| 170 | Manuka | 51.73 | 4.55 | 43.73 |
| 171 | Manuka | 45.21 | 10.49 | 44.29 |
| 172 | Manuka | 49.46 | 5.62 | 44.93 |
| 173 | Manuka | 61.04 | 2.64 | 36.37 |
| 174 | Manuka | 66.60 | −6.19 | 39.65 |
| 175 | Manuka | 61.33 | −2.06 | 40.78 |
| 176 | Unknown | 19.15 | 21.02 | 59.85 |
| 177 | Unknown | 11.92 | 45.97 | 42.11 |
| 178 | Unknown | 56/06 | 4.52 | 39.48 |
| 179 | Unknown | 54.80 | 7.16 | 38.10 |
| 180 | Unknown | 4.39 | 76.15 | 19.45 |
| 181 | Unknown | 40.76 | 14.10 | 45.13 |
| 182 | Unknown | 15.64 | 25.84 | 58.50 |
| 183 | Unknown | 10.28 | 28.01 | 61.70 |
| 184 | Unknown | 4.20 | 95.56 | 0.27 |
| 185 | Unknown | 10.08 | 29.07 | 60.84 |
| 186 | Unknown | 16.07 | 7.71 | 76.22 |
| 187 | Unknown | 6.36 | 18.32 | 75.30 |
| 188 | Unknown | 10.26 | 12.25 | 77.48 |

TABLE 3

Predicted floral composition of artificially blended honeys.
Samples assigned numbers 201-314.

| Sample number | Original Sample 1 | Original Sample 2 | Manuka (%) | Kanuka (%) | Pasture (%) |
|---|---|---|---|---|---|
| 201 | 101 | 139 | 27.81 | 9.47 | 62.70 |
| 202 | 102 | 140 | 29.60 | 10.16 | 60.24 |
| 203 | 103 | 141 | 26.63 | 14.09 | 59.26 |
| 204 | 104 | 142 | 16.92 | 11.29 | 71.78 |
| 205 | 105 | 143 | 25.19 | 11.12 | 63.67 |
| 206 | 106 | 144 | 39.72 | 2.21 | 58.11 |
| 207 | 107 | 145 | 24.58 | 12.01 | 63.41 |
| 208 | 108 | 146 | 60.25 | 9.34 | 30.36 |
| 209 | 109 | 148 | 55.21 | 16.71 | 28.04 |
| 210 | 110 | 147 | 54.41 | 9.24 | 36.36 |
| 211 | 111 | 149 | 23.47 | 43.05 | 33.45 |
| 212 | 112 | 150 | 47.63 | 21.37 | 31.00 |
| 213 | 113 | 151 | 20.33 | 47.06 | 32.59 |
| 214 | 114 | 152 | 35.50 | 31.65 | 32.84 |
| 215 | 115 | 153 | 37.69 | 33.74 | 28.54 |
| 216 | 116 | 154 | 33.16 | 46.62 | 20.17 |
| 217 | 117 | 155 | 20.10 | 42.89 | 36.95 |
| 218 | 118 | 156 | 33.72 | 47.68 | 18.55 |
| 219 | 119 | 157 | 15.60 | 56.07 | 28.32 |
| 220 | 120 | 158 | 24.54 | 14.98 | 60.47 |
| 221 | 121 | 159 | 26.01 | 15.28 | 58.70 |
| 222 | 122 | 160 | 20.23 | 19.96 | 59.80 |
| 223 | 123 | 161 | 14.36 | 31.51 | 54.10 |
| 224 | 124 | 162 | 17.04 | 25.22 | 57.73 |
| 225 | 125 | 163 | 15.90 | 26.05 | 58.03 |
| 226 | 126 | 164 | 5.60 | 73.44 | 20.97 |
| 227 | 127 | 165 | 7.14 | 76.34 | 16.53 |
| 228 | 128 | 166 | 18.58 | 50.94 | 30.50 |
| 229 | 129 | 167 | 5.27 | 75.01 | 19.73 |
| 230 | 130 | 168 | 21.18 | 56.10 | 22.73 |
| 231 | 131 | 169 | 11.35 | 74.24 | 14.43 |
| 232 | 132 | 170 | 20.04 | 29.82 | 50.13 |
| 233 | 133 | 171 | 29.53 | 24.70 | 45.77 |
| 234 | 134 | 172 | 29.62 | 17.13 | 53.26 |
| 235 | 135 | 173 | 27.35 | 22.62 | 50.04 |
| 236 | 136 | 174 | 38.88 | 0.41 | 60.74 |
| 237 | 137 | 175 | 32.78 | 5.96 | 61.28 |
| 238 | 138 | 101 | 28.31 | 12.30 | 59.38 |
| 239 | 159 | 101 | 37.15 | 13.76 | 49.08 |
| 240 | 160 | 102 | 46.83 | 11.72 | 41.45 |
| 241 | 161 | 103 | 37.49 | 20.05 | 42.44 |
| 242 | 162 | 104 | 24.20 | 21.87 | 53.94 |
| 243 | 163 | 105 | 35.97 | 17.49 | 46.52 |
| 244 | 164 | 106 | 43.68 | 20.88 | 35.48 |
| 245 | 165 | 107 | 22.16 | 25.04 | 52.79 |
| 246 | 166 | 108 | 71.75 | 19.64 | 8.60 |
| 247 | 167 | 109 | 53.14 | 26.44 | 20.37 |
| 248 | 168 | 110 | 68.80 | 12.69 | 18.52 |

TABLE 3-continued

Predicted floral composition of artificially blended honeys. Samples assigned numbers 201-314.

| Sample number | Original Sample 1 | Original Sample 2 | Manuka (%) | Kanuka (%) | Pasture (%) |
|---|---|---|---|---|---|
| 249 | 169 | 111 | 37.11 | 6.63 | 56.27 |
| 250 | 170 | 112 | 67.67 | 4.10 | 28.26 |
| 251 | 171 | 113 | 41.56 | 10.08 | 48.36 |
| 252 | 172 | 114 | 60.95 | 4.67 | 34.40 |
| 253 | 173 | 115 | 65.42 | 1.82 | 32.79 |
| 254 | 174 | 116 | 69.15 | 5.10 | 25.73 |
| 255 | 175 | 117 | 49.30 | 7.67 | 43.01 |
| 256 | 129 | 118 | 31.41 | 51.83 | 16.73 |
| 257 | 130 | 119 | 11.30 | 56.63 | 32.07 |
| 258 | 131 | 120 | 11.18 | 63.84 | 25.00 |
| 259 | 132 | 121 | 13.31 | 31.45 | 55.23 |
| 260 | 133 | 122 | 21.60 | 28.78 | 49.62 |
| 261 | 134 | 123 | 9.77 | 26.72 | 63.49 |
| 262 | 135 | 124 | 7.91 | 32.92 | 59.15 |
| 263 | 136 | 125 | 10.24 | 16.21 | 73.53 |
| 264 | 137 | 126 | 2.76 | 56.44 | 40.81 |
| 265 | 138 | 127 | 13.43 | 60.53 | 26.08 |
| 266 | 139 | 128 | 12.73 | 42.20 | 45.08 |
| 267 | 140 | 151 | 5.90 | 41.95 | 52.13 |
| 268 | 141 | 152 | 6.45 | 44.39 | 49.14 |
| 269 | 142 | 153 | 8.32 | 35.49 | 56.16 |
| 270 | 143 | 154 | 1.97 | 53.53 | 44.48 |
| 271 | 144 | 155 | 11.23 | 33.08 | 55.67 |
| 272 | 145 | 156 | 16.00 | 46.40 | 37.61 |
| 273 | 146 | 157 | 10.69 | 48.34 | 40.97 |
| 274 | 147 | 158 | 27.90 | 14.59 | 57.53 |
| 275 | 148 | 150 | 20.04 | 30.25 | 49.71 |
| 276 | 149 | 101 | 36.36 | 29.59 | 34.03 |
| 277 | 101 | 102 | 58.14 | 5.92 | 35.94 |
| 278 | 103 | 104 | 39.91 | 6.84 | 53.26 |
| 279 | 105 | 106 | 59.78 | 1.95 | 38.29 |
| 280 | 107 | 108 | 69.98 | 5.23 | 24.77 |
| 281 | 109 | 110 | 98.50 | 13.67 | -12.27 |
| 282 | 111 | 112 | 62.47 | 0.56 | 36.98 |
| 283 | 113 | 114 | 56.84 | 6.68 | 36.46 |
| 284 | 115 | 116 | 75.14 | 5.04 | 19.77 |
| 285 | 117 | 118 | 50.24 | 19.69 | 29.93 |
| 286 | 119 | 120 | 29.34 | 10.10 | 60.55 |
| 287 | 121 | 122 | 24.01 | 18.19 | 57.78 |
| 288 | 123 | 124 | 9.84 | 28.05 | 62.09 |
| 289 | 125 | 126 | -0.97 | 69.09 | 31.87 |
| 290 | 127 | 128 | 13.87 | 73.66 | 12.51 |
| 291 | 129 | 130 | -5.21 | 100.19 | 5.03 |
| 292 | 131 | 132 | -1.89 | 81.27 | 20.62 |
| 293 | 133 | 134 | 16.42 | 34.13 | 49.45 |
| 294 | 135 | 136 | 7.71 | 24.94 | 67.34 |
| 295 | 137 | 138 | 10.52 | 16.00 | 73.47 |
| 296 | 139 | 140 | 9.23 | 10.84 | 79.91 |
| 297 | 141 | 142 | 8.20 | 16.24 | 75.53 |
| 298 | 143 | 144 | 11.45 | 8.53 | 80.02 |
| 299 | 145 | 146 | 20.78 | 11.44 | 67.78 |
| 300 | 147 | 148 | 27.71 | 10.89 | 61.44 |
| 301 | 149 | 150 | 13.63 | 60.54 | 25.78 |
| 302 | 151 | 152 | 7.61 | 71.25 | 21.12 |
| 303 | 153 | 154 | 2.55 | 76.87 | 20.56 |
| 304 | 155 | 156 | 12.17 | 71.50 | 16.34 |
| 305 | 157 | 158 | 14.90 | 52.98 | 32.12 |
| 306 | 159 | 160 | 23.66 | 17.45 | 58.89 |
| 307 | 161 | 162 | 20.91 | 34.58 | 44.50 |
| 308 | 163 | 164 | 23.44 | 27.93 | 48.61 |
| 309 | 165 | 166 | 19.55 | 36.75 | 43.69 |
| 310 | 167 | 168 | 33.30 | 25.23 | 41.48 |
| 311 | 169 | 170 | 39.92 | 8.14 | 51.95 |
| 312 | 171 | 172 | 45.33 | 8.67 | 46.00 |
| 313 | 173 | 174 | 57.40 | 0.29 | 42.36 |
| 314 | 175 | 174 | 60.83 | -3.38 | 42.60 |

The model building process was iterative, that is, predictions from the outcome of a round of modelling were fed back into the model as original estimates, and predictions recalculated. This was done to refine the original estimates, which were based on intuitive 'off-the-top-of-the-head' assessments using constituent compositional analyses (abundance of certain constituent markers correlating to honeys and nectars of known floral origin. The iterative refinement process reduces model variance, or 'trains the model', by adjusting the floral compositional weightings. This process is similar to the supervised learning refinement of neural network models, particularly associated with pattern recognition with systems containing high levels of noise or variation. This process ultimately results in a library or 'training set' of known honeys, generated from a large set of samples with a variety of floral origins, to be used to generate predictions on compositions of unknown samples from their respective fluorescent EEM data. Note that this iteratively trained data set is the basis for all further comparisons described in this report.

Model Validation

First, to validate the model, a sample or set of samples were used with a known composition. A working model should accurately predict the composition. Therefore, manual tests were conducted using a form of independent sample validation: every tenth sample (samples 110, 120, 130, etc.) were excluded from the model and the model remade with all honeys except these excluded samples. The excluded samples were then fed back in to the model as unknowns to test whether they yielded the same predicted outcomes as when they were originally part of the model. This comparison was made by comparing predicted values for those samples against the predicted floral composition from the model made with all honeys. This revealed that the prediction was accurate to a mean square residual error (rmse) of 2.72% (FIG. 1). The maximum difference between trained and predicted outcomes was 8.09% (Table 4).

Predicting Floral Origin of Unknown Samples

After validating the model, 13 truly unknown samples (for which no compositional or floral data was known) were loaded into the model and predictions were made without any original knowledge of the composition. The results predicted by the full scan model are displayed in Table 5.

TABLE 4

Validation of the accuracy of the model

| Sample number | Trained data composition | | | Validation data | | | Differences | | |
|---|---|---|---|---|---|---|---|---|---|
| | Manuka (%) | Kanuka (%) | Pasture (%) | Manuka (%) | Kanuka (%) | Pasture (%) | Manuka (%) | Kanuka (%) | Pasture (%) |
| 110 | 78.06 | 8.02 | 13.85 | 77.95 | 8.00 | 13.97 | 0.10 | 0.02 | -0.13 |
| 120 | 27.87 | 7.33 | 64.78 | 27.76 | 7.25 | 64.97 | 0.11 | 0.08 | -0.19 |

TABLE 4-continued

Validation of the accuracy of the model

| Sample number | Trained data composition | | | Validation data | | | Differences | | |
|---|---|---|---|---|---|---|---|---|---|
| | Manuka (%) | Kanuka (%) | Pasture (%) | Manuka (%) | Kanuka (%) | Pasture (%) | Manuka (%) | Kanuka (%) | Pasture (%) |
| 130 | −8.16 | 111.49 | −3.32 | −7.97 | 111.57 | −3.60 | −0.20 | −0.09 | 0.28 |
| 140 | 8.74 | 8.39 | 82.85 | 8.52 | 8.22 | 83.25 | 0.22 | 0.17 | −0.39 |
| 150 | 14.27 | 47.28 | 38.40 | 13.99 | 47.05 | 38.91 | 0.28 | 0.24 | −0.51 |
| 160 | 26.46 | 16.77 | 56.76 | 26.40 | 16.74 | 56.85 | 0.06 | 0.03 | −0.09 |
| 170 | 51.73 | 4.55 | 43.73 | 51.78 | 4.62 | 43.62 | −0.05 | −0.07 | 0.11 |
| 180 | 28.01 | 9.13 | 62.85 | 25.19 | 11.10 | 63.69 | 2.82 | −1.98 | −0.84 |
| 190 | 44.89 | 34.05 | 21.01 | 37.62 | 33.65 | 28.70 | 7.27 | 0.41 | −7.69 |
| 200 | 18.46 | 29.67 | 51.84 | 16.05 | 26.18 | 57.75 | 2.41 | 3.49 | −5.91 |
| 210 | 32.07 | 22.08 | 45.87 | 27.38 | 22.62 | 50.01 | 4.69 | −0.54 | −4.14 |
| 220 | 24.47 | 24.37 | 51.15 | 22.08 | 24.97 | 52.94 | 2.39 | −0.60 | −1.79 |
| 230 | 50.31 | 10.68 | 38.97 | 49.27 | 7.55 | 43.15 | 1.03 | 3.13 | −4.18 |
| 240 | 5.33 | 61.08 | 33.60 | 13.41 | 60.46 | 26.16 | −8.09 | 0.62 | 7.44 |
| 250 | 18.45 | 31.25 | 50.29 | 19.96 | 30.17 | 49.87 | −1.51 | 1.09 | 0.41 |
| 260 | 49.67 | 20.07 | 30.10 | 50.40 | 19.73 | 29.73 | −0.73 | 0.34 | 0.37 |
| 270 | 9.69 | 15.20 | 75.10 | 10.50 | 15.98 | 73.51 | −0.81 | −0.78 | 1.59 |
| 280 | 14.83 | 53.59 | 31.57 | 14.83 | 52.94 | 32.23 | −0.01 | 0.66 | −0.66 |

TABLE 5

Predictions of unknown honey sample compositions using a full scan and three excitation wavelengths.

| Sample number | Predictions using a full scan | | | Predictions using 3 excitation wavelengths | | | Differences | | |
|---|---|---|---|---|---|---|---|---|---|
| | Manuka (%) | Kanuka (%) | Pasture (%) | Manuka (%) | Kanuka (%) | Pasture (%) | Manuka (%) | Kanuka (%) | Pasture (%) |
| 1 | 19.15 | 21.02 | 59.85 | 19.18 | 18.44 | 62.4 | −0.03 | 2.58 | −2.54 |
| 2 | 11.92 | 45.97 | 42.11 | 10.98 | 46.89 | 42.13 | 0.95 | −0.92 | −0.02 |
| 3 | 56.06 | 4.52 | 39.48 | 55.24 | 3.53 | 41.27 | 0.81 | 0.99 | −1.79 |
| 4 | 54.80 | 7.16 | 38.10 | 54.38 | 7.46 | 38.2 | 0.42 | −0.31 | −0.10 |
| 5 | 4.39 | 76.15 | 19.45 | 5.19 | 73.54 | 21.24 | −0.80 | 2.61 | −1.80 |
| 6 | 40.76 | 14.10 | 45.13 | 41.06 | 14.23 | 44.7 | −0.30 | −0.13 | 0.43 |
| 7 | 15.64 | 25.84 | 58.50 | 17.26 | 24.02 | 58.69 | −1.62 | 1.82 | −0.19 |
| 8 | 10.28 | 28.01 | 61.70 | 10.23 | 23.98 | 65.76 | 0.05 | 4.03 | −4.07 |
| 9 | 4.20 | 95.56 | 0.27 | 6.01 | 90.25 | 3.76 | −1.81 | 5.31 | −3.49 |
| 10 | 10.08 | 29.07 | 60.84 | 11.19 | 28.23 | 60.57 | −1.11 | 0.84 | 0.27 |
| 11 | 16.07 | 7.71 | 76.22 | 17.79 | 7.96 | 74.26 | −1.72 | −0.25 | 1.96 |
| 12 | 6.36 | 18.32 | 75.30 | 6.66 | 16.18 | 77.13 | −0.31 | 2.14 | −1.83 |
| 13 | 10.26 | 12.25 | 77.48 | 12.35 | 12.15 | 75.5 | −2.09 | 0.10 | 1.99 |

Example 2

The method was tested to determine whether restricting the analysis to discrete fluorescent peaks ('peak picking') yielded predictions with similar accuracy to the use of the full EEM. Furthermore, if three or four excitation wavelengths could be used instead of full EEM scanning then it would be simpler and cheaper to build a portable instrument for use in the field.

Figure 2:
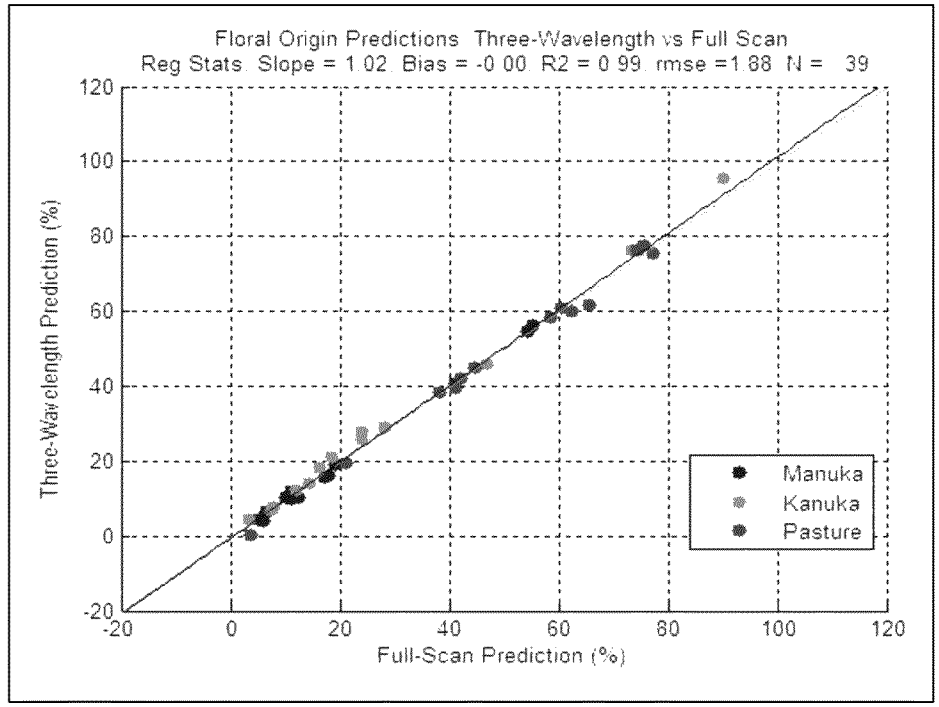
FIG. 2 shows a graph comparison of three-wavelength data with full-scan data for the validated honey samples.
Figure 3:
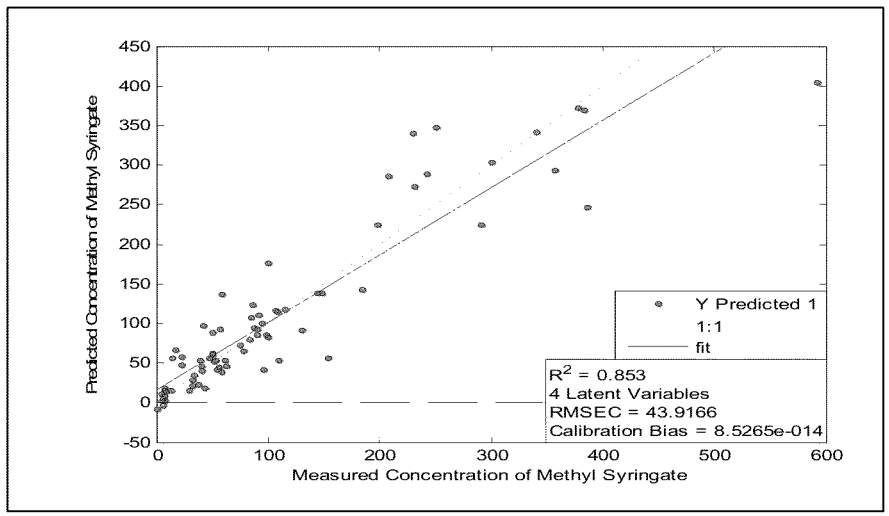
FIG. 3 shows a graph comparison of measured and predicted levels of methyl syringate concentrations, from the EEM data using the NPLS model.
Figure 4:
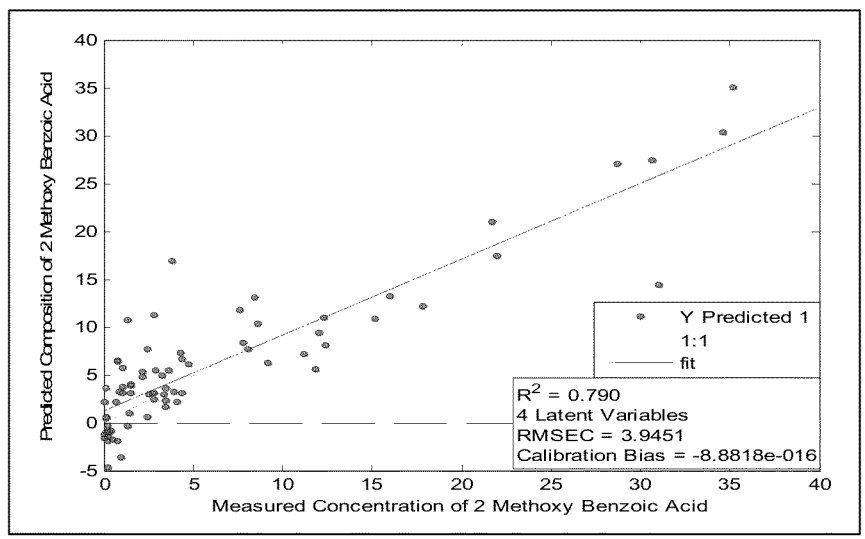
FIG. 4 shows a graph comparison of measured and predicted levels of 2-methoxybenzoic acid concentrations, from the EEM data using the NPLS model.
Figure 5:
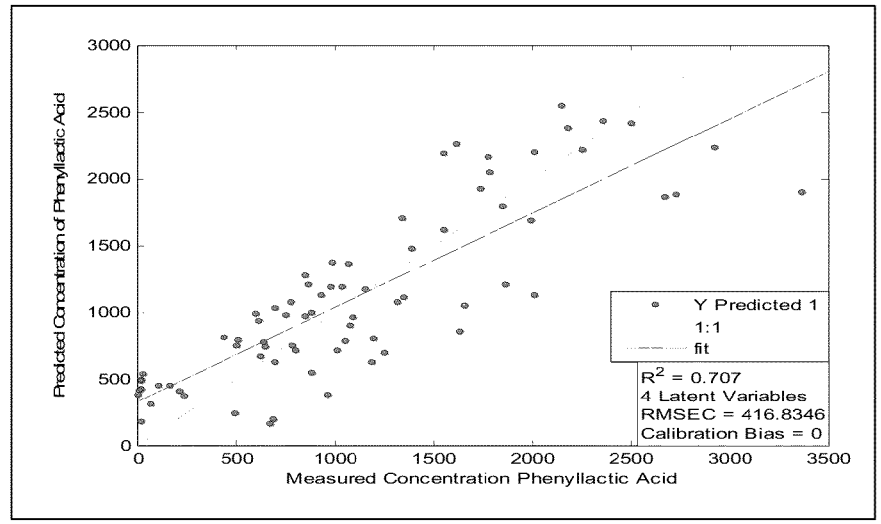
FIG. 5 shows a graph comparison of measured and predicted levels of phenyllactic acid concentrations, from the EEM data using the NPLS model.
Figure 6:
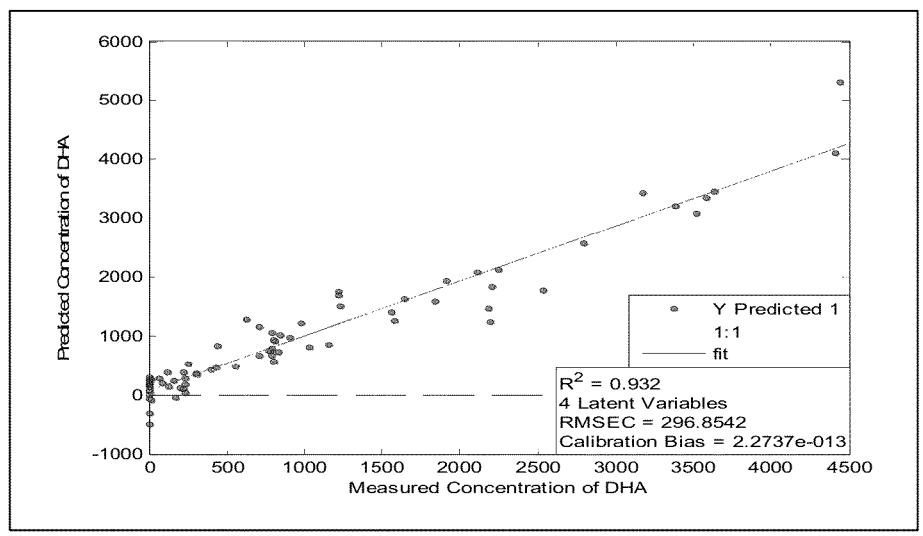
FIG. 6 shows a graph comparison of measured and predicted levels of dihydroxy acetone (DHA) concentrations, from the EEM data using the NPLS model.
Figure 7:
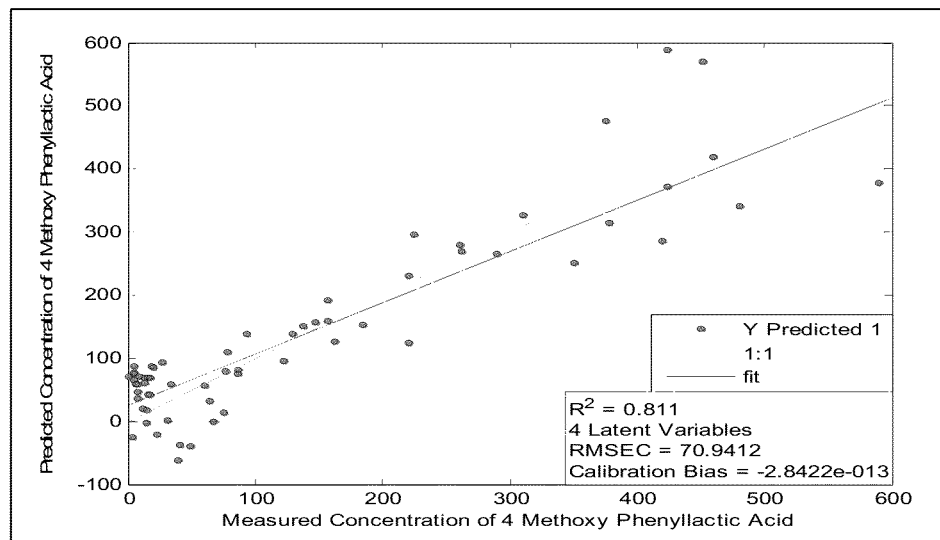
FIG. 7 shows a graph comparison of measured and predicted levels of 4-methoxy phenyllactic acid concentrations, from the EEM data using the NPLS model.
Figure 8:
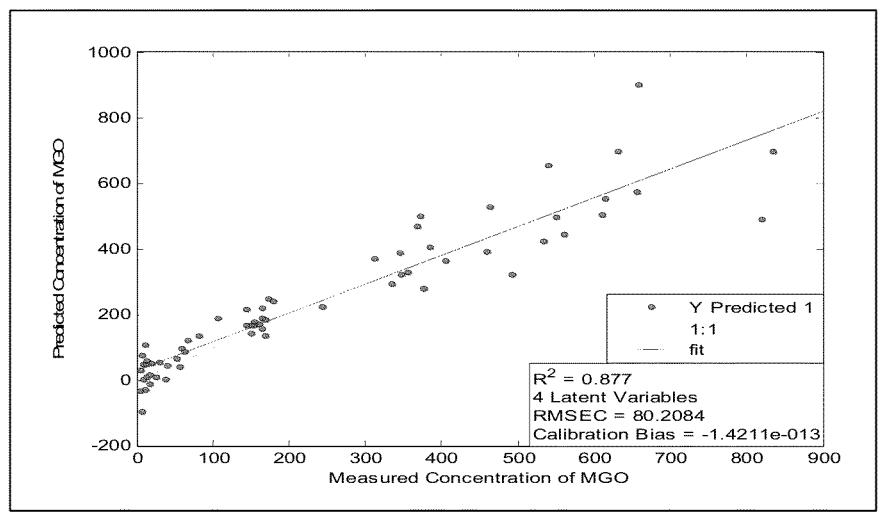
FIG. 8 shows a graph comparison comparing the measured and predicted levels of methylglyoxal (MGO) concentrations, from the EEM data using the NPLS model.
Figure 9:
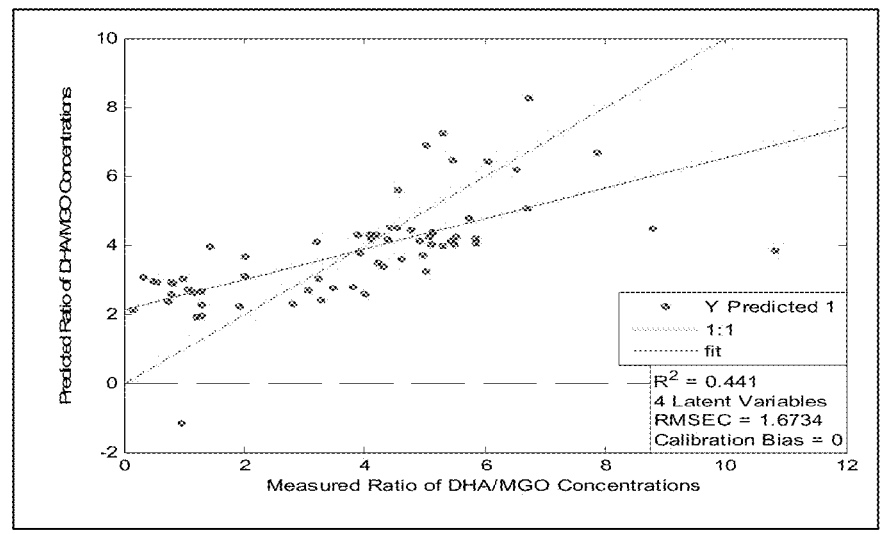
FIG. 9 shows a graph comparison of measured and predicted levels of the ratio between dihydroxy acetone and methyl glyoxal concentrations, from the EEM data using the NPLS model.
Figure 10:
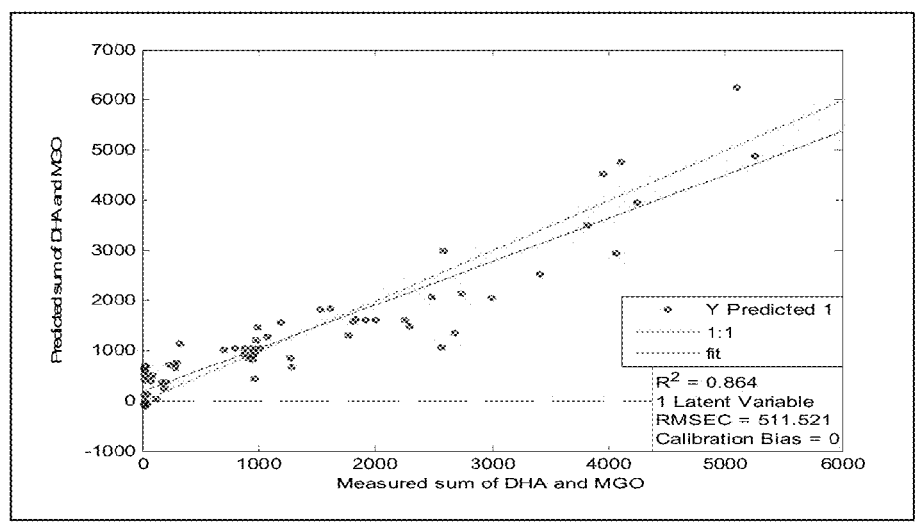
FIG. 10 shows a graph comparison of measured and predicted levels of the sum of dihydroxy acetone (DHA) and methylglyoxal (MGO) concentrations from the EEM data using the NPLS model.

Therefore, the wavelengths chosen were 230, 265 and 335 nm and their emission scans recorded. These excitation wavelengths were chosen as they were the co-ordinates of the main peaks found in manuka and kanuka honeys. Reducing the number of co-ordinates from the original EEM to just three excitation wavelengths resulted in predicted floral origins varying from EEM-based predictions by a mean square residual value of 1.88% (FIG. 2), with the largest individual sample variance being 5.31% (Table 5—see Example 1).

Example 3

The floral composition of a honey may be estimated using the phenolic profile of the honey. The concentrations of the subset of the phenolic and antimicrobial compounds that yield the greatest floral discrimination were identified from the original set of samples used in Example 1.

The NPLS model described in Example 1 was used to correlate EEM profiles with the chemical data of the known honey samples. Of the 75 honey samples, 66 of the honey samples had full discriminatory chemical profiles, with the other 9 honeys lacked the antimicrobial methylglyoxal (MGO) and 4-methoxyphenyllactic acid concentrations. Available chemical data was entered into the model instead of the floral composition data to determine if these chemical data matched the fluorescent EEM profiles. In addition to correlating and comparing individual chemical constituents, the ratio of dihydroxy acetone (DHA, a precursor to MGO) to MGO (which corresponds to the age and maturity of manuka honey and the sum of MGO and its DHA precursor were also compared. MGO is the molecule responsible for the unique antimicrobial activity of the manuka honey, from which the UMF value is derived. It is the UMF value which predominantly determines the monetary value of manuka honey.

There was a correlation ($R2$ above 0.854 using 4 LV) between the fluorescent data and the MGO values, dihydroxy acetone (DHA), and methyl syringate. When the measured concentrations of constituents were plotted against the predictions made by the Toolbox, more than 85% of the concentrations for these constituents was accounted for using NPLS model and fluorescent data (FIGS. 3 to 10).

The correlation between the fluorescence profile and some of the phenolic constituents of the honey is not surprising. However, the correlation between the phenolic profiles and levels of the antimicrobial (UMF®) molecule MGO and its precursor DHA was not entirely expected.

Example 4

In this example, a practical demonstration of honey fluorescence profiling is illustrated.

samples were suspected of stating a higher UMF value than the honey actually possessed or the botanical origin was suspected to not be as per label.

Method

The unknown samples were scanned following the methods outlined in Example 1. The EEMs were then loaded into Matlab and compared with model predictions.

Results

The fluorescence analysis can identify honeys that have been mislabelled. Data in Table 6 present the model's predictions of honey composition, according to their phenolic profiles. The predictions made are similar to the predictions made based on known honey sample phenolic profiles.

TABLE 6

Predictions of compositional data of honey samples bought in Indonesia

| Honey Sample (Manufacturer names removed) | Label Claim | Methyl Syringate | 2 Methoxy Benzoic acid | Phenyl-lactic acid | 4 Methoxy Phenyl-lactic acid | Dihydroxy Acetone | Methyl-glyoxal | UMF by MGO calculator | HMF | Suspected description of honey | % Manuka | % Kanuka | % Pasture |
|---|---|---|---|---|---|---|---|---|---|---|---|---|---|
| 1 | 25+ | 271 | 1.1 | 1230 | 65.2 | 175 | 143 | 6.7 | 36 | Aged kanuka, some manuka content | −1.61 | 85.99 | 15.62 |
| 2 | 18+ | 136 | 1.5 | 470 | 50.8 | 0 | 8 | na | 450 | Heated kanuka/pasture blend | 24.03 | 46.07 | 29.97 |
| 3 | 20+ | 109 | 5.7 | 943 | 16.3 | 124 | 402 | 12.6 | 156 | Suspect manuka/kanuka/pasture | 63.93 | 0.78 | 35.38 |
| 4 | 8+ | 79.3 | 3.6 | 684 | 14.1 | 418 | 320 | 10.8 | 17 | Manuka/kanuka/pasture blend | 33.75 | 11.83 | 54.44 |
| 5 | 25+ | 17.1 | 143 | 1600 | 9.1 | 1310 | 1219 | 26.5 | 34 | Suspect manuka | 51.38 | 2.80 | 45.86 |
| 6 | 20+ | 293 | 63.2 | 608 | 5.7 | 1030 | 1054 | 24.2 | 83 | Suspect manuka/pasture | 87.98 | −3.28 | 15.23 |
| 7 | 30+ | 41.1 | 2.8 | 501 | 5.2 | 445 | 281 | 9.9 | 24 | Manuka/pasture blend | 30.93 | 10.38 | 58.69 |
| 8 | 30+ | 27.3 | 3 | 595 | 3.5 | 629 | 290 | 10.1 | 31 | Manuka/pasture blend | 40.30 | 3.59 | 56.13 |
| 9 | 15+ | 176 | 1.8 | 608 | 63.8 | 106 | 61 | 4.7 | 12 | Kanuka/pasture blend, some manuka content | 2.63 | 86.08 | 11.29 |
| 10 | 25+ | 30.4 | 115 | 1410 | 8.4 | 328 | 863 | 21.3 | 200 | Suspect manuka | 57.05 | −4.65 | 47.67 |

After the model was created as described in Example 1, the model was tested to ensure that the model could identify mislabelled honeys.

A batch of 10 samples (and some constituent concentration data) were tested having been sourced from commercial honey products on sale in the Indonesian market. These In conclusion, the floral composition of unknown honeys could be predicted. These predictions matched the phenolic profiles of the honeys. Their phenolic profiles determined that the honeys did not match their labelled origins. Further the analysis showed that the stated UMF activity was not always true to label. Further HMF levels detected using the method showed that some of the honeys had been heated. Therefore, fluorescence-based analysis allows rapid determination of mislabelled honeys.

Example 5

The effect of pH on the fluorescence of the honey samples was investigated.

The optimal range of the Dylight dyes and AF 594 is from pH 4 to 9. Previous studies on honeys have shown that the pH of the honey used in previous trials ranged from pH 3 to 5.

The pH of the honeys tested in earlier examples for fluorescence was tested to determine if the pH was within the optimal range of the dye. This would ensure that an accurate reading of the dye was taken. The pH of all the honey samples in this set was measured in the diluted concentration (2% w/v). This showed that the samples analysed in this set all ranged from pH 3.8 to 5.6 with only two samples having a pH under 4.0. Therefore, no modification of the pH was deemed necessary.

Example 6

It is understood by the applicants that inconsistent intensity levels seen for the peak located at 590 nm excitation and 620 nm emission may be due to fluorescence quenching.

Fluorescence quenching involves a decrease in fluorescence intensity. Quenching is heavily dependent on pressure, temperature and can be a result of many processes such as excited state reactions, energy transfer, collisional quenching and complex formation. Molecular $O_2$ and iodine are common chemical quenchers. A probable cause of quenching is due to Dexter (collisional energy transfer). This could be due to the dye and the honey molecules colliding so that non-fluorescent compounds absorb the energy from excited state molecules and it is instead used in vibrational movement or heat. This is a phenomenon that is short ranged and dependent on the overlap of the molecular orbitals.

The presence of the honey in a solution may change the hydrophobicity of the dye. If the dye is more hydrophobic it is more likely to stack together and exclude the water molecules. This could also change the fluorescent properties.

In previous experiments all the samples were run at 2% (w/v) honey and 0.05% (v/v) Alexa Fluor 594. A lower concentration might decrease the effects of quenching as there would be a larger spacing between molecules, so less orbital overlap between molecules.

The aim of this experiment was to determine if using a lower concentration of honey and dye would reduce the effects of quenching.

Method

A honey sample (kanuka honey, sample number 122 above) was randomly chosen. A set of subsamples was made using varying concentrations of dye, honey and different machine settings (Table A).

TABLE 9

Composition of subsamples and instrument settings.

| Sub-sample number | Concentration of honey (% (w/v)) | Concentration of dye (% (v/v)) | Gain |
|---|---|---|---|
| 1 | 2 | 0.05 | 85 |
| 2 | 1 | 0.025 | 90 |
| 3 | 0.6666 | 0.01666 | 100 |
| 4 | 0.5 | 0.0125 | 100 |
| 5 | 0.3333 | 0.0083 | 100 |
| 6 | 0.2 | 0.005 | 100 |
| 7 | 0.1 | 0.0025 | 130 |
| 8 | 10 | 0.25 | 85 |
| 9 | 5 | 0.125 | 85 |
| 10 | 3.333 | 0.0833 | 85 |
| 11 | 2.5 | 0.0625 | 85 |
| 12 | 0.25 | 0.00625 | 90 |
| 13 | 0.2 | 0.005 | 110 |
| 14 | 0.3333 | 0.0083 | 110 |
| 15 | 0.1666 | 0.00416 | 110 |
| 16 | 0.125 | 0.003125 | 110 |

Results

Figure 11:
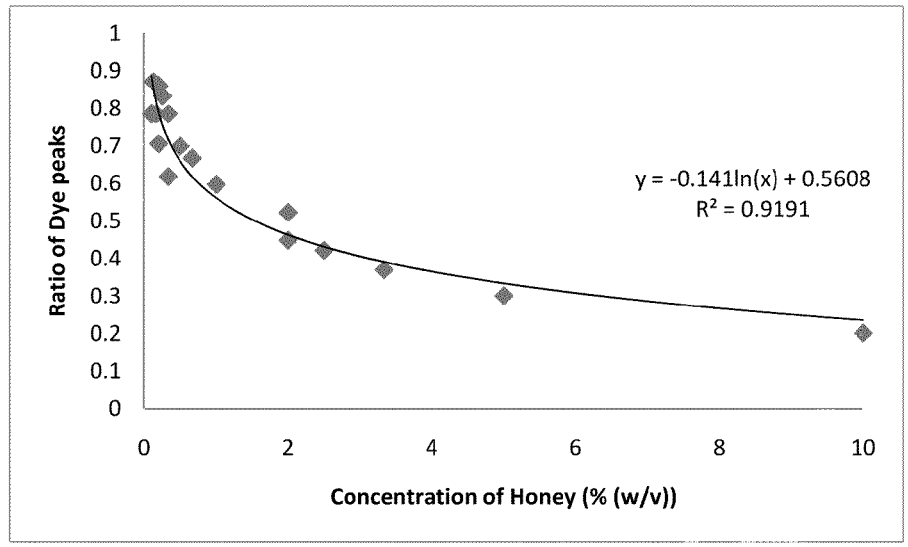
FIG. 11 shows an example of the changing ratio of the two dye peaks (265,615 and 590,620) as the concentration of honey in a solution changes.

The ratio of the two peaks from the dye was used to analyse the effect of quenching. When there is a lower concentration of honey in the solution the ratio is decreased (FIG. 11). There is an apparently logarithmic relationship between ratio of the dye peaks and the concentration of the dye and honey.

When the concentration of honey is less than 0.33% (w/v) the shape of the honey spectra changes. Below this level, the peak at 265 excitation, 275 emission—an important co-ordinate required for analysis and differentiation of honeys—no longer displayed a shoulder.

A strong quenching effect is seen at high concentrations of honey. At concentrations above 2% (w/v), honey peaks display similar-shaped profiles to those seen in previous experiments that used 2% (w/v).

Figure 12:
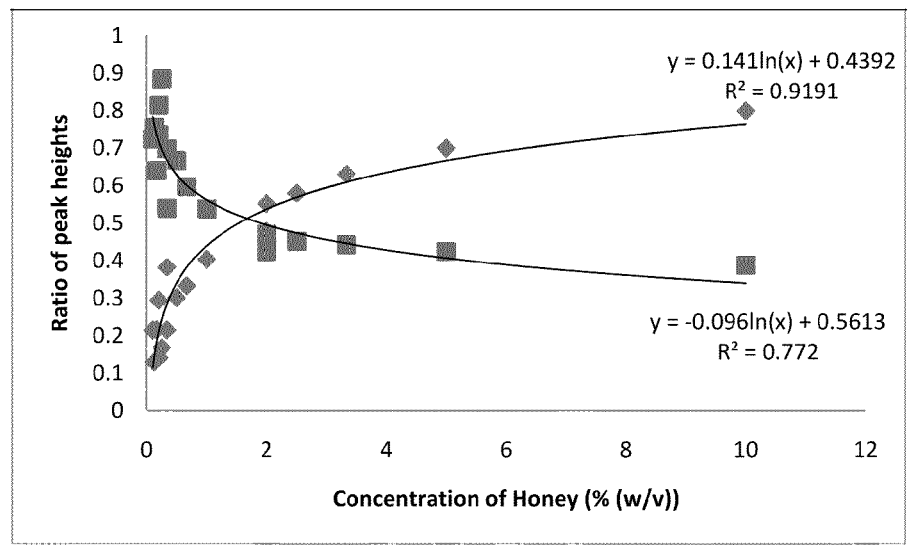
FIG. 12 shows an example of the changing ratio of two honey peaks (red) and the inverse of two dye peaks (blue) as the concentration of honey in a solution changes.

Therefore, as there was no more detail seen at higher concentrations of honey, the maximum concentration of honey was considered to be 2%. However, when the honey concentration is decreased, the ratio between the two heights of the honey peaks (230,310 and 265,375) also starts to change (FIG. 12).

Conclusion

A 0.2% to 5% concentration may be used, more specifically 1.5 to 2.5%, and optionally 2% (w/v) honey solution may be used, provided the correct balance between minimising the affects of quenching but also retaining important coordinates of the honey fluorescence, and would continue to be used in the analysis of honey samples by fluorescence, with a 0.05% Alexa Fluor Dye 594 solution.

Example 7

Photo bleaching of honey samples was investigated. As noted above, the Alexa Dye 594 is not photo stable, as was shown by a 30% decrease in intensity after 24 h of exposure to sunlight in our trials completed by the applicants.

Method

Two randomly selected honey samples were chosen, a manuka (102) and a kanuka (126). Each honey was analysed in diluted and undiluted form, after either being stored for 4 h in the dark or 4 h under lights with an intensity of 650 µmol. The diluted samples were diluted in deionised water to 2% (w/v) samples and stored in a volume of 0.5 mL for consistency. Duplicates of each samples were recorded and the average taken.

Results

Figure 13:
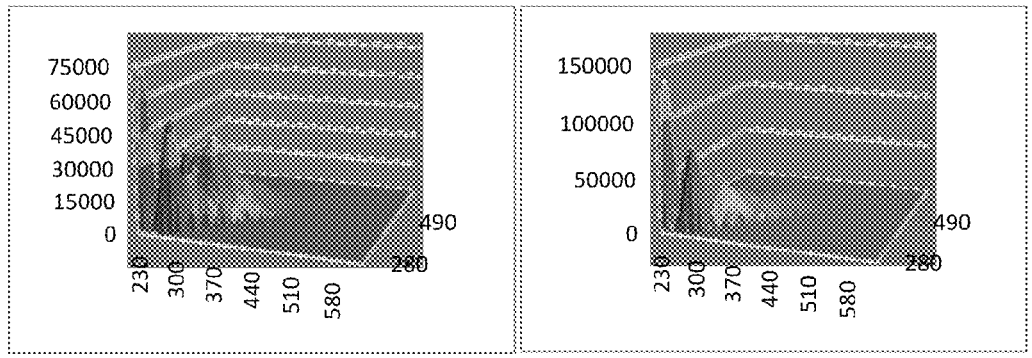
FIG. 13 illustrates a comparison scan between diluted kanuka honeys exposed to light (left) and stored in the dark (right)

When the diluted kanuka was exposed to light, the overall intensity level almost halved (FIG. 13). When bleached in the light, there is a change in shape of the profile of the kanuka honey from the unbleached honey. Peaks emerge at 250,380 250,440 and 250,500. Closer inspection of the unbleached spectrum showed that in the other spectra, these are observed as peak shoulders—peaks that are obscured from view by larger peaks with similar co-ordinates. Therefore, the compound that fluoresces in this region is not subject to being bleached by the light.

Figure 14:
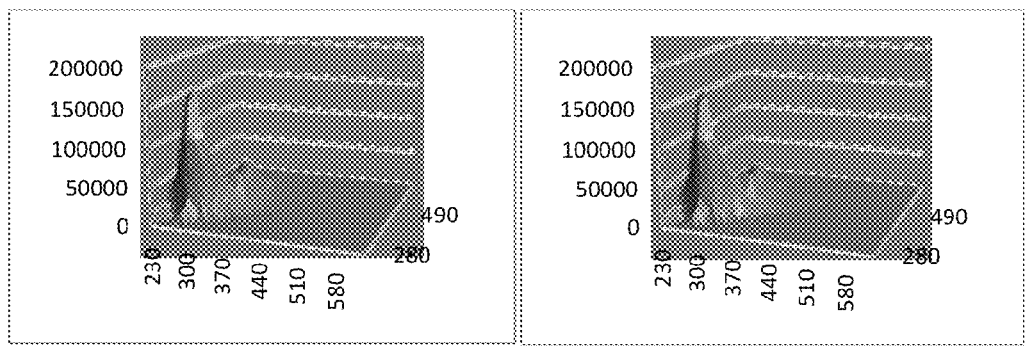
FIG. 14 illustrates a comparison scan between concentrated manuka honeys exposed to light (left) and stored in the dark (right)
Figure 15:
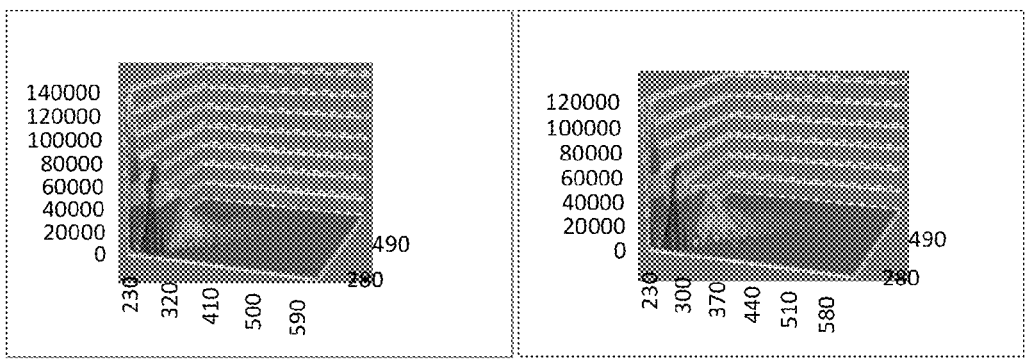
FIG. 15 illustrates a comparison scan between concentrated kanuka honeys exposed to light (left) and stored in the dark (right)
Figure 16:
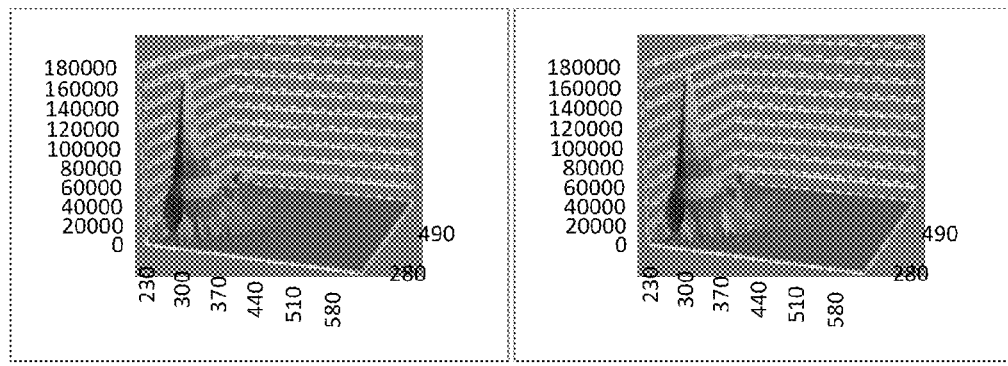
FIG. 16 illustrates a comparison scan between diluted manuka honeys exposed to light (left) and stored in the dark (right)

No photo bleaching occurred in the diluted manuka honey or the concentrated samples (FIGS. 14-16). These had consistent intensity levels and profile shapes.

Conclusions

It is proposed by the applicants that, as long as the diluted samples are not exposed to sunlight for periods of time exceeding those presented here, photo bleaching is not considered a significant problem.

Example 8

Honey is concentrated nectar. Therefore, many of the phenolic constituents of honey are present in nectar. Previous work found that the nectar samples had similar fluorescent profiles to older, more mature honeys. This experiment aimed to determine if nectar samples of 100% manuka origin generated a similar profile to that of a 100% manuka honey sample.

Methods

Thirteen nectar samples supplied were diluted to 4% (w/v) solution, diluted in a 0.05% (v/v) solution of Alexa Fluor 594 dye. These were scanned as described in earlier examples.

Results

Varying peak shapes and locations were seen in the fluorescent spectrum recorded from nectar samples.

Figure 17:
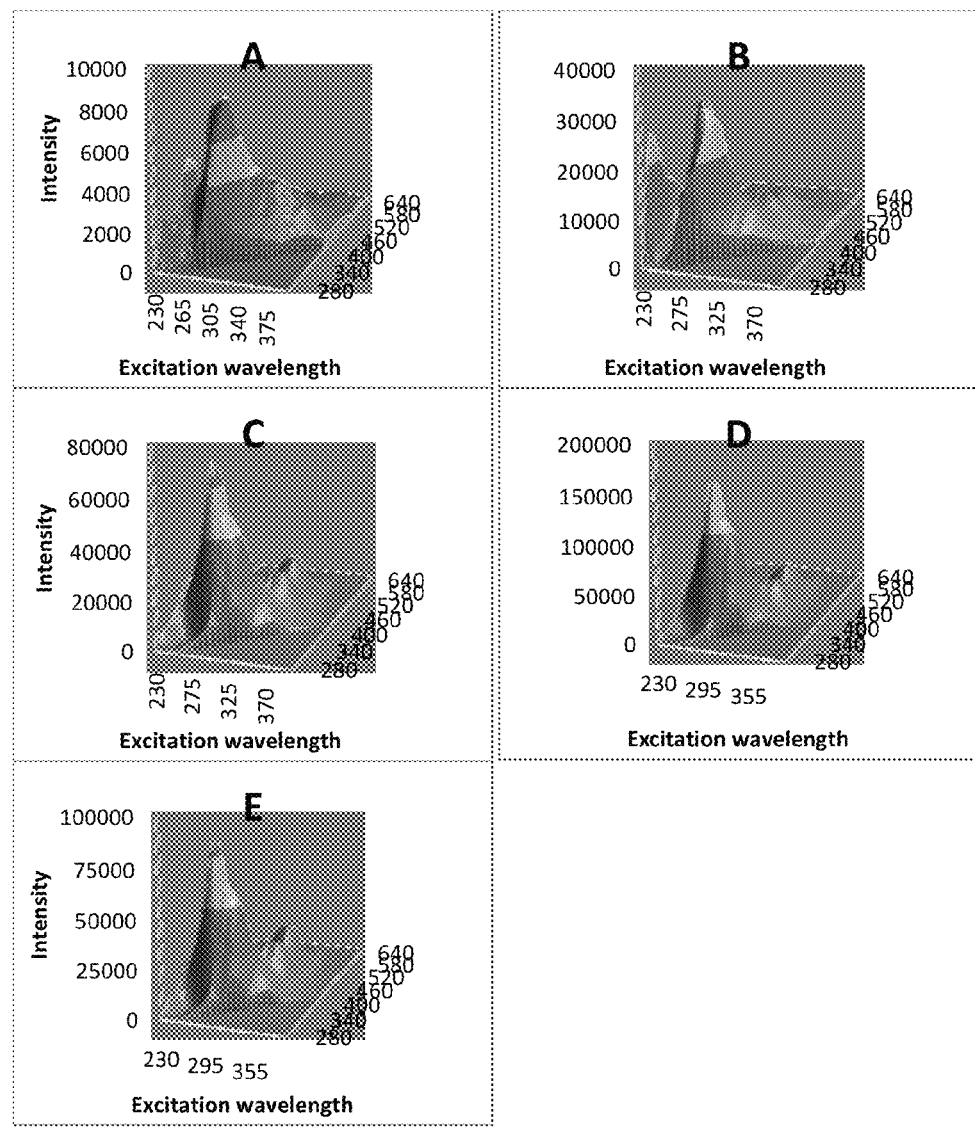
FIG. 17 illustrates fluorescence spectra of wild nectar samples. A:NF, B:BS, C:WB, D:Rh1, E:Rh2.

The fluorescence spectrum of the wild nectars (FIG. 17) showed that Sites A and B yielded slightly non-characteristic profiles whereas Sites C, D and E had profile shapes characteristic of manuka honeys.

Figure 18:
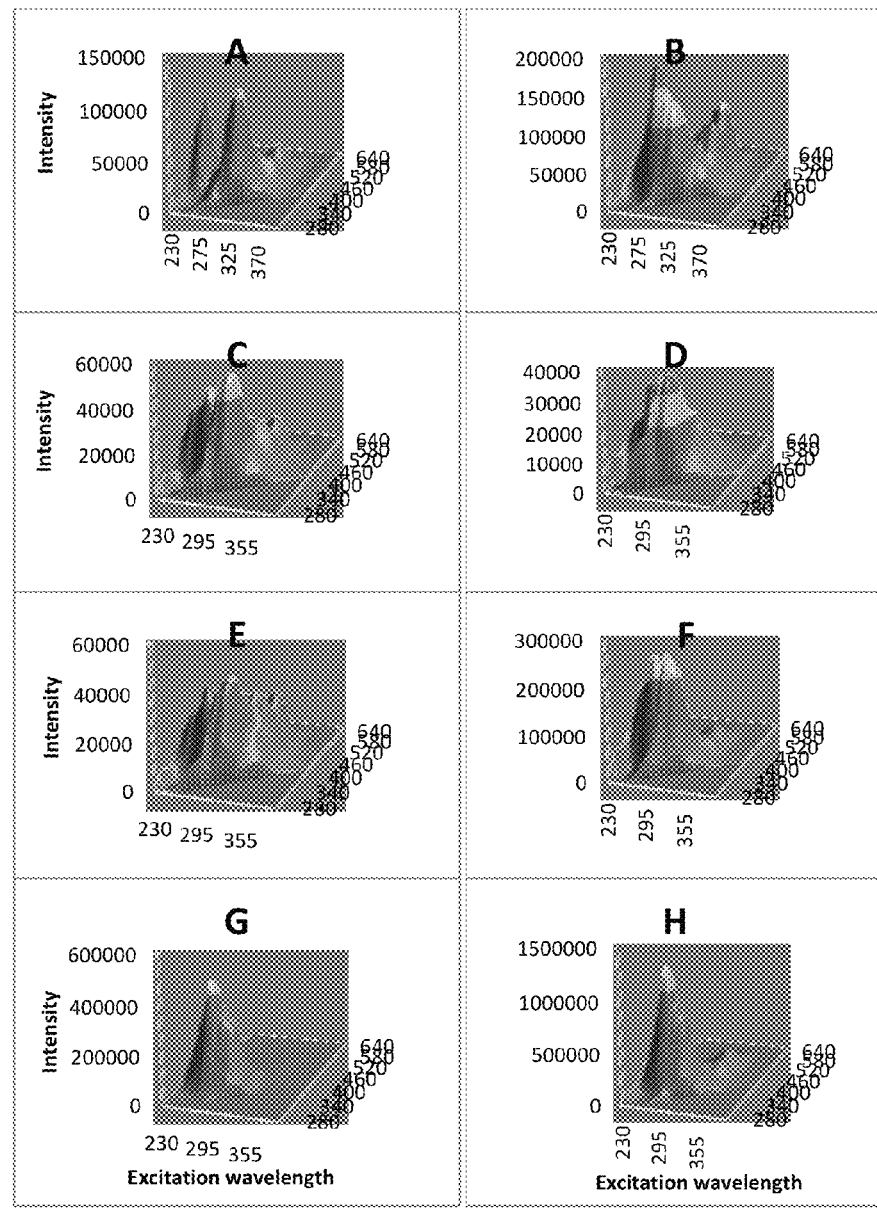
FIG. 18 illustrates the fluorescence spectra from nectar samples collected in a glasshouse. A: *Leptospermum scoparium* var. incanum, B: *Leptospermum scoparium* var. 'West Coast South Island' (un-named), C: *Leptospermum scoparium* var. incanum cultivar, D: *Leptospermum scoparium* var. 'triketone" cultivar (probably contains some var. incanum parentage), E: *Leptospermum scoparium* var. incanum cultivar, F: *Leptospermum spectabile* cultivar (Australian species), G: *Leptospermum polygalifolium* (Australian Species), H: *Leptospermum continentale* (Australian species)

The fluorescence spectra that were obtained from nectar samples that were collected in a glasshouse had a variety of shapes (FIG. 18). Sample A had a strong peak at 245,385, which had not been associated with manuka honeys before. This could be due to contamination or something that needs to be further explored. Samples C and E are cultivars of the same species as Sample A. These two spectra had very similar shapes and intensity levels but were not the same as Sample A.

Figure 19:
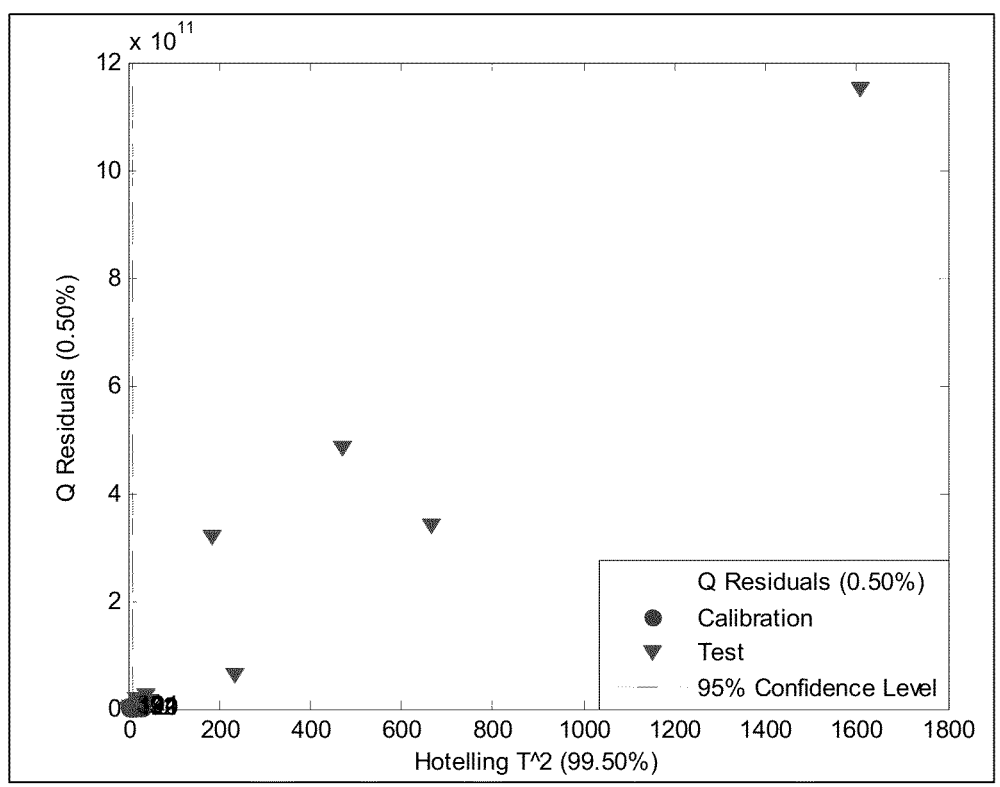
FIG. 19 illustrates hotelling T2 vs. Q residuals plot plotting the honey samples as the calibration set and the nectar samples as the test set.

When the nectar samples were compared against the honey samples in the model made in Section 3, the nectar samples were identified as outliers in the hotelling $T_2$ vs. Q residuals plot (FIG. 19). The intensity levels of the fluorescence spectra cannot be compared to that of the honey samples as the concentrations of these samples differed and, therefore, the nectar samples were outliers when the models were compared.

Nectar samples had fluorescence EEM determined with a 4% (w/v) solution.

Conclusion

In most cases, the fluorescent profiles resembled those of their corresponding honeys and it was the applicants finding that by standardising concentrations or developing a model that standardises fluorescent intensities, any further variations could be overcome.

Aspects of the methods and device have been described by way of example only and it should be appreciated that modifications and additions may be made thereto without departing from the scope of the claims herein.

What is claimed is:

1. A method for determining the concentration values of key constituent chemicals of honey, comprising the steps of:
    (a) estimating the botanical origin of at least one standard honey sample, by:
        (i) obtaining key constituent chemical concentrations; and
        (ii) assigning the botanical origin as a numerical value on the basis of abundance of chemical compounds characteristic of certain botanical groups, wherein the numerical value is capable of reflecting an estimation that the standard honey sample includes honey from more than one botanical origin;
    (b) generating the fluorescence signature of standard honey samples, by:
        (i) exciting a diluted honey sample solution with light of wavelengths over the range 200-700 nm at increasing wavelength increments; and
        (ii) measuring the intensity of the fluorescent light emitted from the excited solution over the range 280-650 nm at increasing wavelength increments; and
        (iii) measuring the wavelength of the fluorescent light emitted from the excited solution over the range 280-650 nm at increasing wavelength increments; and
        (iv) combining excitation and emitted light as 2-dimensional excitation-emission matrix (EEM);
    (c) constructing a validated predictive mathematical model from standard honey data, by:
        (i) using the botanical origin value determined in step (a) as the first matrix in a multivariate analysis;
        (ii) using the fluorescence EEM data determined in step (b) as the second matrix in a multivariate analysis;
        (iii) generating a mathematical model using these two matrices; and,
        (iv) establishing a statistical confidence of predictive power of mathematical model with leave-one-out validation process;
    (d) generating the fluorescence EEM signature of an unknown honey sample or samples, as outlined in step (b); and
    (e) using the unknown honey fluorescence EEM data from step (d) with the validated mathematical model of step (c) to predict and assign concentration values of key constituent chemicals of honey with defined statistical confidence.

2. The method as claimed in claim 1 wherein the numerical value of botanical origin is expressed as a percentage manuka honey, percentage kanuka honey, percentage other specific floral origin honey, percentage other origin honey as a sum, or combinations thereof.

3. The method as claimed in claim 1 wherein the constituent chemicals in a honey and/or the honey floral origin are determined instead by analysis of the nectar from which the honey is derived.

4. The method as claimed in claim 1 wherein the fluorescence signature is generated using excitation wavelengths in the range 200-700 nm.

5. The method as claimed in claim 1 wherein the fluorescence signature is generated using the key excitation wavelengths, 230 nm, 265 nm, and 335 nm.

6. The method as claimed in claim 1 wherein the leave-one-out validation process uses a partial least squares (PLS) analysis.

7. The method as claimed in claim 1 wherein the key constituent chemical include compounds selected from the group consisting of: methyl syringate, 2-methoxybenzoic acid, phenyllactic acid, 4-methoxyphenyllactic acid, dihydroxyacetone, methylglyoxal, and combinations thereof.

8. The method as claimed in claim 1 wherein the sample or samples are initially diluted to a 0.2 to 5% w/v solution using water.

9. The method as claimed in claim 1 wherein the method is used to identify the concentration of manuka, kanuka and other floral origin honey in a honey sample.

10. The method as claimed in claim 1 wherein the method is used to determine the UMF® activity of a honey sample.

11. A method for determining the botanical origin of honey including the steps of:
   (a) estimating the botanical origin of standard honey samples, by:
       (i) obtaining key constituent chemical concentrations; and
       (ii) assigning the botanical origin as a numerical value on the basis of abundance of chemical compounds characteristic of certain botanical groups, wherein the numerical value is capable of reflecting an estimation that the standard honey sample includes honey from more than one botanical origin;
   (b) generating the fluorescence signature of standard honey samples, by:
       (i) exciting a diluted honey sample solution with light of wavelengths over the range 200-700 nm at increasing wavelength increments; and
       (ii) measuring the intensity of the fluorescent light emitted from the excited solution over the range 280-650 nm at increasing wavelength increments; and
       (iii) measuring the wavelength of the fluorescent light emitted from the excited solution over the range 280-650 nm at increasing wavelength increments; and
       (iv) combining excitation and emitted light as 2-dimensional excitation-emission matrix (EEM);
   (c) constructing a validated predictive mathematical model from standard honey data, by:
       (i) using the botanical origin value determined in step (a) as the first matrix in a multivariate analysis;
       (ii) using the fluorescence EEM data determined in step (b) as the second matrix in a multivariate analysis;
       (iii) generating a mathematical model using these two matrices; and,
       (iv) establishing a statistical confidence of predictive power of mathematical model with leave-one-out validation process;
   (d) generating the fluorescence EEM signature of an unknown honey sample or samples, as outlined in step (b); and
   (e) using the unknown honey fluorescence EEM data from step (d) with the validated mathematical model of step (c) to predict and assign numerical value of botanical origin of honey with defined statistical confidence.

12. The method as claimed in claim 11 wherein the numerical value of botanical origin is expressed as a percentage manuka honey, percentage kanuka honey, percentage other specific floral origin honey, percentage other origin honey as a sum, or combinations thereof.

13. The method as claimed in claim 11 wherein the constituent chemicals in a honey and/or the honey floral origin are determined instead by analysis of the nectar from which the honey is derived.

14. The method as claimed in claim 11 wherein the fluorescence signature is generated using excitation wavelengths in the range 200-700 nm.

15. The method as claimed in claim 11 wherein the fluorescence signature is generated using the key excitation wavelengths, 230 nm, 265 nm, and 335 nm.

16. The method as claimed in claim 11 wherein the key constituent chemical include compounds selected from the group consisting of: methyl syringate, 2-methoxybenzoic acid, phenyllactic acid, 4-methoxyphenyllactic acid, dihydroxyacetone, methylglyoxal, and combinations thereof.

17. The method as claimed in claim 11 wherein the sample or samples are initially diluted to a 0.2 to 5% w/v solution using water.

18. The method as claimed in claim 11 wherein the method is used to identify the concentration of manuka, kanuka and other floral origin honey in a honey sample.

19. The method as claimed in claim 11 wherein the method is used to determine the UMF® activity of a honey sample.

\* \* \* \* \*